(12) United States Patent
Redei

(10) Patent No.: US 10,093,981 B2
(45) Date of Patent: Oct. 9, 2018

(54) COMPOSITIONS AND METHODS FOR IDENTIFYING DEPRESSIVE DISORDERS

(71) Applicant: Northwestern University, Evanston, IL (US)

(72) Inventor: Eva E. Redei, Chicago, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 15/727,181

(22) Filed: Oct. 6, 2017

(65) Prior Publication Data

US 2018/0057884 A1 Mar. 1, 2018

Related U.S. Application Data

(60) Continuation-in-part of application No. 14/598,975, filed on Jan. 16, 2015, now abandoned, and a continuation-in-part of application No. 15/296,807, filed on Oct. 18, 2016, now Pat. No. 9,951,387, which is a continuation of application No. 14/994,802, filed on Jan. 13, 2016, now Pat. No. 9,469,875, which is a division of application No. 13/276,565, filed on Oct. 19, 2011, now abandoned.

(60) Provisional application No. 61/928,723, filed on Jan. 17, 2014, provisional application No. 62/041,443, filed on Aug. 25, 2014, provisional application No. 62/042,022, filed on Aug. 26, 2014, provisional application No. 61/394,449, filed on Oct. 19, 2010.

(51) Int. Cl.
| | |
|---|---|
| C07H 21/02 | (2006.01) |
| C12Q 1/6883 | (2018.01) |
| G01N 33/68 | (2006.01) |

(52) U.S. Cl.
CPC ....... *C12Q 1/6883* (2013.01); *G01N 33/6893* (2013.01); *C12Q 2600/156* (2013.01); *C12Q 2600/158* (2013.01); *G01N 2800/304* (2013.01); *G01N 2800/60* (2013.01); *H05K 999/99* (2013.01)

(58) Field of Classification Search
None
See application file for complete search history.

(56) References Cited

U.S. PATENT DOCUMENTS

| | | | |
|---|---|---|---|
| 5,011,769 A | 4/1991 | Duck et al. |
| 5,124,246 A | 6/1992 | Urdea et al. |
| 5,130,238 A | 7/1992 | Malek et al. |
| 5,210,884 A | 5/1993 | Redford |
| 5,270,184 A | 12/1993 | Walker et al. |
| 5,283,174 A | 2/1994 | Arnold, Jr. et al. |
| 5,288,609 A | 2/1994 | Engelhardt et al. |
| 5,399,491 A | 3/1995 | Kacian et al. |
| 5,403,711 A | 4/1995 | Walder et al. |
| 5,409,818 A | 4/1995 | Davey et al. |
| 5,455,166 A | 10/1995 | Walker |
| 5,538,848 A | 7/1996 | Livak et al. |
| 5,624,802 A | 4/1997 | Urdea et al. |
| 5,660,988 A | 8/1997 | Duck et al. |
| 5,695,934 A | 12/1997 | Brenner |
| 5,710,029 A | 1/1998 | Ryder et al. |
| 5,710,264 A | 1/1998 | Urdea et al. |
| 5,714,330 A | 2/1998 | Brenner et al. |
| 5,750,341 A | 5/1998 | Macevicz |
| 5,792,614 A | 8/1998 | Western et al. |
| 5,814,447 A | 9/1998 | Ishiguro et al. |
| 5,824,518 A | 10/1998 | Kacian et al. |
| 5,846,717 A | 12/1998 | Brow et al. |
| 5,849,481 A | 12/1998 | Urdea et al. |
| 5,851,770 A | 12/1998 | Babon et al. |
| 5,882,867 A | 3/1999 | Ullman et al. |
| 5,914,230 A | 6/1999 | Liu et al. |
| 5,925,517 A | 7/1999 | Tyagi et al. |
| 5,928,862 A | 7/1999 | Morrison |
| 5,958,692 A | 9/1999 | Cotton et al. |
| 5,985,557 A | 11/1999 | Prudent et al. |
| 5,994,069 A | 11/1999 | Hall et al. |
| 6,001,567 A | 12/1999 | Brow et al. |
| 6,013,170 A | 1/2000 | Meade |
| 6,063,573 A | 5/2000 | Kayyem |
| 6,090,543 A | 7/2000 | Prudent et al. |
| 6,110,677 A | 8/2000 | Western et al. |
| 6,110,684 A | 8/2000 | Kemper et al. |
| 6,121,001 A | 9/2000 | Western et al. |
| 6,150,097 A | 11/2000 | Tyagi et al. |
| 6,183,960 B1 | 2/2001 | Lizardi |
| 6,221,583 B1 | 4/2001 | Kayyem et al. |
| 6,235,502 B1 | 5/2001 | Weissman et al. |
| 6,248,229 B1 | 6/2001 | Meade |

(Continued)

FOREIGN PATENT DOCUMENTS

| | | |
|---|---|---|
| WO | WO 00/018957 | 4/2000 |
| WO | WO 2006084132 | 8/2006 |

OTHER PUBLICATIONS

The Mammalian Gene Collection (https://genecollections.nci.nih.gov/MGC/ last updated Mar. 2009 and accessed online Jun. 1, 2018).*

Adessi et al., Solid phase DNA amplification: characterisation of primer attachment and amplification mechanisms, Nucleic Acid Res. 2010; 28:E87.

Altamura et al., Age at onset and latency to treatment (duration of untreated illness) in patients with mood and anxiety disorders: a naturalistic study. Int Clin Psychopharmacol 2010; 25: 172-9.

(Continued)

*Primary Examiner* — Amanda Haney
(74) *Attorney, Agent, or Firm* — Casimir Jones SC; David W. Staple

(57) ABSTRACT

Provided herein are compositions, kits, and methods for the identification of depressive disorders. In particular, provided herein are compositions, kits, and methods for the detection or diagnosis of major depressive disorder.

1 Claim, 1 Drawing Sheet
Specification includes a Sequence Listing.

(56) References Cited

U.S. PATENT DOCUMENTS

| | | | |
|---|---|---|---|
| 6,303,305 | B1 | 10/2001 | Wittwer et al. |
| 6,306,597 | B1 | 10/2001 | Macevicz |
| 6,432,360 | B1 | 8/2002 | Church |
| 6,485,944 | B1 | 11/2002 | Church et al. |
| 6,511,803 | B1 | 1/2003 | Church et al. |
| 6,534,274 | B2 | 3/2003 | Becker et al. |
| 6,541,205 | B1 | 4/2003 | Yokoyama et al. |
| 6,787,308 | B2 | 9/2004 | Balasubramanian et al. |
| 6,833,246 | B2 | 12/2004 | Balasubramanian |
| 7,323,305 | B2 | 1/2008 | Leamon et al. |
| 7,374,885 | B2 | 5/2008 | Becker et al. |
| 8,679,789 | B2 | 3/2014 | Arnold et al. |
| 2005/0042638 | A1 | 2/2005 | Arnold et al. |
| 2005/0130173 | A1 | 6/2005 | Leamon et al. |
| 2006/0046265 | A1 | 3/2006 | Becker et al. |
| 2012/0094859 | A1 | 4/2012 | Redei et al. |
| 2015/0218639 | A1 | 8/2015 | Redei |

OTHER PUBLICATIONS

Andrus et al., Gene expression patterns in the hippocampus and amygdala of endogenous depression and chronic stress models. Molecular psychiatry 2012; 17: 49-61.

Barnay, Genetic disease detection and DNA amplification using cloned thermostable ligase, Proc. Natl. Acad. Sci USA 1991; 88:189-93.

Belmaker et al., Major depressive disorder. The New England journal of medicine 2008; 358: 55-68.

Belzeaux et al., Responder and nonresponder patients exhibit different peripheral transcriptional signatures during major depressive episode. Transl Psychiatry. Nov. 13, 2012;2:e185.

Benjamini et al., Controlling the False Discovery Rate—a Practical and Powerful Approach to Multiple Testing. J Roy Stat Soc B Met 1995; 57: 289-300.

Carter et al., The relationship of demographic, clinical, cognitive and personality variables to the discrepancy between self and clinician rated depression. J Affect Disord 2010; 124: 202-6.

Chinnaiyan et al., Mechanisms of enhanced radiation response following epidermal growth factor receptor signaling inhibition by erlotinib (Tarceva), Cancer Res 2005; 65:3328-35.

Cohen, Statistical Power Analysis for the Behavioral Sciences. 2nd ed. Hillsdale: L Erlbaum Associates; 1988, TOC only, 4 pages.

Cross-Disorder Group of the Psychiatric Genomics Consortium. Identification of risk loci with shared effects on five major psychiatric disorders: a genome-wide analysis. Lancet 2013; 381:1371-9.

Cuijpers et al., The effects of psychotherapies for major depression in adults on remission, recovery and improvement: A meta-analysis. J Affect Disorders 2014; 159:118-126.

Desmond et al., The Telephone Interview for Cognitive Status (TICS): Reliability and validity in a stroke sample. International Journal of Geriatric Psychiatry 1994; 9: 803-7.

Eady et al., Variation in gene expression profiles of peripheral blood mononuclear cells from healthy volunteers. Physiological genomics 2005; 22: 402-11.

Ferrari et al.,Burden of depressive disorders by country, sex, age, and year: findings from the global burden of disease study 2010. PLoS Med 2013; 10: e1001547.

Gaiteri et al., Beyond modules and hubs: the potential of gene coexpression networks for investigating molecular mechanisms of complex brain disorders. Genes, brain, and behavior 2014; 13: 13-24.

Guatelli et al., Isothermal, in vitro amplification of nucleic acids by a multienzyme reaction modeled after retroviral replication, Proc. Natl. Acad. Sci. USA 1990; 87: 1874-1878.

Gunther et al., Prediction of clinical drug efficacy by classification of drug-induced genomic expression profiles in vitro. Proceedings of the National Academy of Sciences of the United States of America 2003; 100: 9608-13.

Hamilton, A rating scale for depression. Journal of Neurology, Neurosurgery, and Psychiatry 1960; 23: 56-62.

Hardeveld et al., Prevalence and predictors of recurrence of major depressive disorder in the adult population. Acta psychiatrica Scandinavica 2010; 122: 184-91.

Hidaka, Depression as a disease of modernity: explanations for increasing prevalence. J Affect Disord 2012; 140: 205-14.

Huerta-Ramirez et al., Diagnosis delay in first episodes of major depression: a study of primary care patients in Spain. J Affect Disord 2013; 150: 1247-50.

Kessler et al., Lifetime prevalence and age-of-onset distributions of DSM-IV disorders in the National Comorbidity Survey Replication. Arch Gen Psychiatry 2005; 62: 593-602.

Kurian et al., Identification of blood biomarkers for psychosis using convergent functional genomics. Molecular psychiatry 2011; 16: 37-58.

Kwoh et al., Transcription-based amplification system and detection of amplified human immunodeficiency virus type 1 with a bead-based sandwich hybridization format, Proc. Natl. Acad. Sci. USA1989; 86:1173-1177.

Le-Niculescu et al., Identifying blood biomarkers for mood disorders using convergent functional genomics. Molecular psychiatry 2009; 14: 156-74.

Lepine et al., He increasing burden of depression. Neuropsychiatr Dis Treat 2011; 7: 3-7.

Leuchter et al., Comparative effectiveness of biomarkers and clinical indicators for predicting outcomes of SSRI treatment in Major Depressive Disorder: results of the BRITE-MD study. Psychiatry Res 2009; 169: 124-31.

Licino et al., Launching the 'war on mental illness'. Molecular psychiatry 2014; 19: 1-5.

Licino et al., Pharmacogenomics of antidepressant treatment effects. Dialogues Clin Neurosci 2011; 13: 63-71.

Liew et al., The peripheral blood transcriptome dynamically reflects system wide biology: a potential diagnostic tool. J Lab Clin Med 2006; 147: 126-32.

Liotti et al., Unmasking disease-specific cerebral blood flow abnormalities: mood challenge in patients with remitted unipolar depression. Am J Psychiatry 2002; 159: 1830-40.

Lizardi et al., Exponential Amplification of Recombinant-RNA Hybridization Probes, Nature BioTechnol. 1988; 6: 1197-1202.

MacArthur Foundation's Initiative on Depression and Primary Care. The MacArthur Initiative on Depression and Primary Care at Dartmouth and Duke: Depression Management Toolkit. Hanover, NH: Dartmouth; 2004, 44 pages.

MacLean et al., Application of 'next-generation' sequencing technologies to microbial genetics, Nature Rev. Microbiol. 2009, 7: 287-296.

The Mammalian Gene Collection, https://genecollections.nci.nih.gov/MGC/ lased updated Mar. 2009; accessed May 1, 2017, 2 pages.

Margulies et al.,Genome sequencing in microfabricated high-density picolitre reactors, Nature. 2005; 437(7057):376-80.

Mehta et al., Gene expression studies in major depression. Curr Psychiatry Rep 2010; 12: 135-44.

Menke et al., Dexamethasone stimulated gene expression in peripheral blood is a sensitive marker for glucocorticoid receptor resistance in depressed patients. Neuropsychopharmacology : official publication of the American College of Neuropsychopharmacology 2012; 37: 1455-64.

Menke, Gene expression: biomarker of antidepressant therapy? Int Rev Psychiatry 2013; 25: 579-91.

Mitra et al., Fluorescent in situ sequencing on polymerase colonies, 2003, Anal Biochem. Sep. 1, 2003;320(1):55-65.

Mohr et al. Effect of telephone-administered vs face-to-face cognitive behavioral therapy on adherence to therapy and depression outcomes among primary care patients: a randomized trial. JAMA, 2012; 307: 2278-85.

Mohr et al., The effect of telephone-administered psychotherapy on depression and attrition: A meta-analysis. Clin Psych Sci & Pract 2008; 15:143-253.

(56) References Cited

OTHER PUBLICATIONS

Mohr et al., The peripheral-blood transcriptome: new insights into disease and risk assessment. Trends in Molecular Medicine 2007; 13: 422-32.

Nelson et al., Detection of Acridinium Esters by Chemiluminescence, Nonisotopic Probing, Blotting, and Sequencing, ch. 17, Larry J. Kricka ed., 2d ed., 1995, pp. 391-428.

Padmos et al., A discriminating messenger RNA signature for bipolar disorder formed by an aberrant expression of inflammatory genes in monocytes. Arch Gen Psychiatry 2008; 65: 395-407.

Pajer et al., Discovery of blood transcriptomic markers for depression in animal models and pilot validation in subjects with early-onset major depression. Transl Psychiatry 2012; 2: e101.

Papakostas et al., Assessment of a multi-assay, serum-based biological diagnostic test for major depressive disorder: a pilot and replication study. Molecular psychiatry 2013; 18: 332-9.

Pence et al., The depression treatment cascade in primary care: a public health perspective. Curr Psychiatry Rep 2012; 14: 328-35.

Pepe et al., Estimation and Comparison of Receiver Operating Characteristic Curves. Stata J 2009; 9: 1.

Persing, "In Vitro Nucleic Acid Amplification Techniques" in Diagnostic Medical Microbiology: Principles and Applications (Persing et al., Eds.), pp. 51-87 (American Society for Microbiology, Washington, DC (1993).

Radich et al., Individual-specific variation of gene expression in peripheral blood leukocytes. Genomics 2004; 83: 980-8.

Riedel et al., Response and remission criteria in major depression—a validation of current practice. J Psychiatr Res 2010; 44: 1063-8.

Rollins et al., Analysis of whole genome biomarker expression in blood and brain. Am J Med Genet B Neuropsychiatr Genet 2010; 153B: 919-36.

Rubin et al., Overexpression, amplification, and androgen regulation of TPD52 in prostate cancer, Cancer Res. 2004;64(11):3814-22.

Segal et al., Antidepressant monotherapy vs sequential pharmacotherapy and mindfulness-based cognitive therapy, or placebo, for relapse prophylaxis in recurrent depression. Arch Gen Psychiatry 2010; 67: 1256-64.

Segman et al., Blood mononuclear cell gene expression signature of postpartum depression. Molecular psychiatry 2010; 15: 93-100, 2.

Sheehan et al., The Mini-International Neuropsychiatric Interview (M.I.N.I.): the development and validation of a structured diagnostic psychiatric interview for DSM-IV and ICD-10. J Clin Psychiatry 1998; 59 Suppl 20: 22-33;quiz 4-57.

Shendure et al., Accurate multiplex polony sequencing of an evolved bacterial genome, Science. 2005; 309(5741):1728-32.

Shyn et al., Novel loci for major depression identified by genome-wide association study of Sequenced Treatment Alternatives to Relieve Depression and meta-analysis of three studies. Molecular psychiatry 2011; 16: 202-15.

Spijker et al., Stimulated gene expression profiles as a blood marker of major depressive disorder. Biological psychiatry 2010; 68: 179-86.

Storey et al., Statistical significance for genomewide studies. Proceedings of the National Academy of Sciences 2003; 100: 9440-5.

Sullivan et al., Evaluating the comparability of gene expression in blood and brain. Am J Med Genet B Neuropsychiatr Genet 2006; 141B: 261-8.

Ten Doesschate et al.,Prediction of recurrence in recurrent depression: a 5.5-year prospective study. J Clin Psychiatry 2010; 71: 984-91.

Voelkerding et al., Next-generation sequencing: from basic research to diagnostics, Clin Chem. Apr. 2009;55(4):641-58.

Walker et al., Isothermal in vitro amplification of DNA by a restriction enzyme/DNA polymerase system, Proc Natl Acad Sci U S A. Jan. 1, 1992;89(1):392-6.

Weiss, Hot prospect for new gene amplifier, Science. Nov. 29, 1991;254(5036):1292-3.

Wray et al., Genome-wide association study of major depressive disorder: new results, meta-analysis, and lessons learned. Molecular psychiatry 2012; 17: 36-48.

* cited by examiner

MDD, Baseline
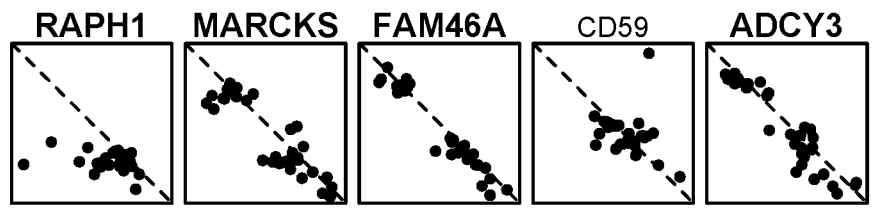
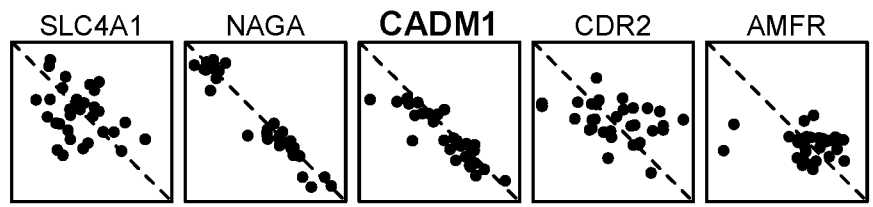
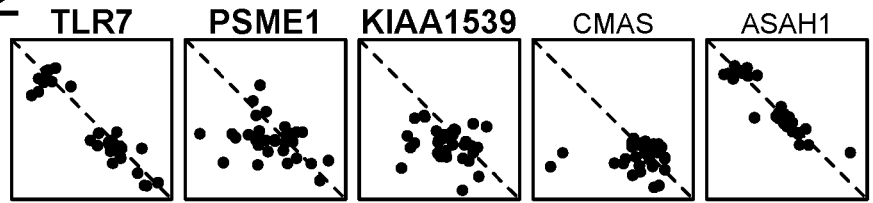
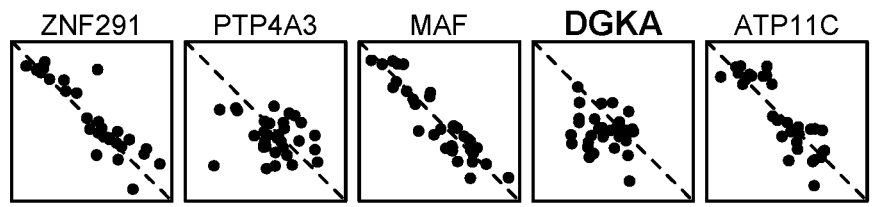

SEQUENCE LISTING

```
<160> NUMBER OF SEQ ID NOS: 40

<210> SEQ ID NO 1
<211> LENGTH: 22
<212> TYPE: DNA
<213> ORGANISM: Homo sapien

<400> SEQUENCE: 1
cgagaacgtc agcatcctct tt                                                22

<210> SEQ ID NO 2
<211> LENGTH: 19
<212> TYPE: DNA
<213> ORGANISM: Homo sapien

<400> SEQUENCE: 2
ggcactgcag gcagaagac                                                    19

<210> SEQ ID NO 3
<211> LENGTH: 23
<212> TYPE: DNA
<213> ORGANISM: Homo sapien

<400> SEQUENCE: 3
cctacacagc ggtcagatag cat                                               23

<210> SEQ ID NO 4
<211> LENGTH: 19
<212> TYPE: DNA
<213> ORGANISM: Homo sapien

<400> SEQUENCE: 4
tcactgcttg gcctttcca                                                    19

<210> SEQ ID NO 5
<211> LENGTH: 23
<212> TYPE: DNA
<213> ORGANISM: Homo sapien

<400> SEQUENCE: 5
tcaacaagct gaccgtatac aca                                               23

<210> SEQ ID NO 6
<211> LENGTH: 21
<212> TYPE: DNA
<213> ORGANISM: Homo sapien

<400> SEQUENCE: 6
cccgcaggta agtttcgaat t                                                 21

<210> SEQ ID NO 7
```

```
<211> LENGTH: 20
<212> TYPE: DNA
<213> ORGANISM: Homo sapien

<400> SEQUENCE: 7
tccatcagtg gtgcaagatg                                              20

<210> SEQ ID NO 8
<211> LENGTH: 20
<212> TYPE: DNA
<213> ORGANISM: Homo sapien

<400> SEQUENCE: 8
ttgaaaatgc aaagcgagtg                                              20

<210> SEQ ID NO 9
<211> LENGTH: 26
<212> TYPE: DNA
<213> ORGANISM: Homo sapien

<400> SEQUENCE: 9
ccaaagctgg gttacaagtg tataac                                       26

<210> SEQ ID NO 10
<211> LENGTH: 21
<212> TYPE: DNA
<213> ORGANISM: Homo sapien

<400> SEQUENCE: 10
gtgacgtcgt tgaaattgca a                                            21

<210> SEQ ID NO 11
<211> LENGTH: 20
<212> TYPE: DNA
<213> ORGANISM: Homo sapien

<400> SEQUENCE: 11
ccgccaacac ttcgtgtatg                                              20

<210> SEQ ID NO 12
<211> LENGTH: 19
<212> TYPE: DNA
<213> ORGANISM: Homo sapien

<400> SEQUENCE: 12
tcagggcttg gctgacctt                                               19

<210> SEQ ID NO 13
<211> LENGTH: 26
<212> TYPE: DNA
<213> ORGANISM: Homo sapien

<400> SEQUENCE: 13
atcttggaaa tgaagtgtct gatgaa                                       26

<210> SEQ ID NO 14
<211> LENGTH: 18
<212> TYPE: DNA
<213> ORGANISM: Homo sapien

<400> SEQUENCE: 14
gcaggagcgc cacttagg                                                18
```

```
<210> SEQ ID NO 15
<211> LENGTH: 20
<212> TYPE: DNA
<213> ORGANISM: Homo sapien

<400> SEQUENCE: 15
acccttccca tgcaaattga                                              20

<210> SEQ ID NO 16
<211> LENGTH: 25
<212> TYPE: DNA
<213> ORGANISM: Homo sapien

<400> SEQUENCE: 16
cttgtgggtg atcttgattg tacag                                        25

<210> SEQ ID NO 17
<211> LENGTH: 23
<212> TYPE: DNA
<213> ORGANISM: Homo sapien

<400> SEQUENCE: 17
ctcacgctca aggaagctta tgt                                          23

<210> SEQ ID NO 18
<211> LENGTH: 26
<212> TYPE: DNA
<213> ORGANISM: Homo sapien

<400> SEQUENCE: 18
ggatataaga ctccatcggt cagagt                                       26

<210> SEQ ID NO 19
<211> LENGTH: 20
<212> TYPE: DNA
<213> ORGANISM: Homo sapien

<400> SEQUENCE: 19
agcaagccag ccacgactat                                              20

<210> SEQ ID NO 20
<211> LENGTH: 23
<212> TYPE: DNA
<213> ORGANISM: Homo sapien

<400> SEQUENCE: 20
cgatttgcct tttagctctg tgt                                          23

<210> SEQ ID NO 21
<211> LENGTH: 24
<212> TYPE: DNA
<213> ORGANISM: Homo sapien

<400> SEQUENCE: 21
ccgtccaagt gaccttattt aacc                                         24

<210> SEQ ID NO 22
<211> LENGTH: 25
<212> TYPE: DNA
<213> ORGANISM: Homo sapien

<400> SEQUENCE: 22
agaagtcaaa ggtcacaagg aacat                                        25
```

<210> SEQ ID NO 23
<211> LENGTH: 19
<212> TYPE: DNA
<213> ORGANISM: Homo sapien

<400> SEQUENCE: 23
cagcggcttc cgagaaaac                                              19

<210> SEQ ID NO 24
<211> LENGTH: 25
<212> TYPE: DNA
<213> ORGANISM: Homo sapien

<400> SEQUENCE: 24
gagtgggctc agttatgaaa aactc                                       25

<210> SEQ ID NO 25
<211> LENGTH: 25
<212> TYPE: DNA
<213> ORGANISM: Homo sapien

<400> SEQUENCE: 25
cctcttggat ctgttgagtt tcttt                                       25

<210> SEQ ID NO 26
<211> LENGTH: 21
<212> TYPE: DNA
<213> ORGANISM: Homo sapien

<400> SEQUENCE: 26
attctcctgt ccgttcgctt t                                           21

<210> SEQ ID NO 27
<211> LENGTH: 20
<212> TYPE: DNA
<213> ORGANISM: Homo sapien

<400> SEQUENCE: 27
agctgagacc aaagttccca                                             20

<210> SEQ ID NO 28
<211> LENGTH: 20
<212> TYPE: DNA
<213> ORGANISM: Homo sapien

<400> SEQUENCE: 28
atcctgaatt ggttcgtgga                                             20

<210> SEQ ID NO 29
<211> LENGTH: 20
<212> TYPE: DNA
<213> ORGANISM: Homo sapien

<400> SEQUENCE: 29
ccgcaatgct tatgctgtgt                                             20

<210> SEQ ID NO 30
<211> LENGTH: 21
<212> TYPE: DNA
<213> ORGANISM: Homo sapien

<400> SEQUENCE: 30
gggcttcttg agcttctcga a                                           21

<210> SEQ ID NO 31
<211> LENGTH: 21
<212> TYPE: DNA
<213> ORGANISM: Homo sapien

<400> SEQUENCE: 31
cccttattga gagcgggatg a                                         21

<210> SEQ ID NO 32
<211> LENGTH: 18
<212> TYPE: DNA
<213> ORGANISM: Homo sapien

<400> SEQUENCE: 32
cgcttctggc ggatgaac                                             18

<210> SEQ ID NO 33
<211> LENGTH: 23
<212> TYPE: DNA
<213> ORGANISM: Homo sapien

<400> SEQUENCE: 33
agcaaggcca gaatggagtc tat                                       23

<210> SEQ ID NO 34
<211> LENGTH: 20
<212> TYPE: DNA
<213> ORGANISM: Homo sapien

<400> SEQUENCE: 34
gtggtgaagg ctgtgaagca                                           20

<210> SEQ ID NO 35
<211> LENGTH: 22
<212> TYPE: DNA
<213> ORGANISM: Homo sapien

<400> SEQUENCE: 35
ggagcttcag tgtctggatg ct                                        22

<210> SEQ ID NO 36
<211> LENGTH: 21
<212> TYPE: DNA
<213> ORGANISM: Homo sapien

<400> SEQUENCE: 36
cgtattcatc ccgaccttcc t                                         21

<210> SEQ ID NO 37
<211> LENGTH: 25
<212> TYPE: DNA
<213> ORGANISM: Homo sapien

<400> SEQUENCE: 37
gctctcttca accagacctc tacat                                     25

<210> SEQ ID NO 38
<211> LENGTH: 23
<212> TYPE: DNA
<213> ORGANISM: Homo sapien

<400> SEQUENCE: 38

```
gtccacattg gaaacaccat ttt                                              23

<210> SEQ ID NO 39
<211> LENGTH: 29
<212> TYPE: DNA
<213> ORGANISM: Homo sapien

<400> SEQUENCE: 39
gcactcataa aactactaaa cagcagagt                                        29

<210> SEQ ID NO 40
<211> LENGTH: 26
<212> TYPE: DNA
<213> ORGANISM: Homo sapien

<400> SEQUENCE: 40
tgtttatctc cagtcgtaga cgatgt                                           26
```

COMPOSITIONS AND METHODS FOR IDENTIFYING DEPRESSIVE DISORDERS

The present application is a continuation-in-part of U.S. patent application Ser. No. 14/598,975, filed Jan. 16, 2015, which claims priority to U.S. Provisional Patent Application No. 61/928,723, filed Jan. 17, 2014; U.S. Provisional Patent Application No. 62/041,443, filed Aug. 25, 2014; and U.S. Provisional Patent Application No. 62/042,022, filed Aug. 26, 2014; each of which is incorporated by reference in their entireties.

The present application is also a continuation-in-part of U.S. patent application Ser. No. 15/296,807, filed Oct. 18, 2016, which is a continuation of U.S. patent application Ser. No. 14/994,802, filed Jan. 13, 2016, now U.S. Pat. No. 9,469,875, which is a divisional of abandoned U.S. patent application Ser. No. 13/276,565, filed Oct. 19, 2011, which claims the priority benefit of U.S. Provisional Patent Application No. 61/394,449, filed Oct. 19, 2010, each of which is incorporated by reference in its entirety.

FIELD OF THE INVENTION

Provided herein are compositions, kits, and methods for the identification of depressive disorders. In particular, provided herein are compositions, kits, and methods for the detection or diagnosis of major depressive disorder.

BACKGROUND OF THE INVENTION

Depressive disorders (e.g. Major depressive disorder (MDD)) are the leading cause of disability in the United States when measured as total time lost to disability, affecting more than 18 million people annually in the USA alone. Depressive disorders, the most common of affective illnesses, include a large set of illnesses ranging from seasonal depressive disorder to chronic depression. There are currently no known available biological markers for depression; diagnosis is made by physicians or psychologists based on structured interviews with the patients. Depressive disorders are among only a few major illnesses that remain reliant upon subjective diagnoses. This contributes to under recognition, trivialization and stigmatization of these disabling illnesses.

MDD treatments (e.g. antidepressants and psychotherapy) carry risks of adverse effects, and the economic cost of inappropriate treatment is high. Conversely, the individual, societal, and economic costs of not identifying and treating MDD is even higher, and include suicide, hospitalization, and/or protracted impairment. The costs of misclassification of MDD for research studies are also significant in wasted dollars, time, and incorrect results.

SUMMARY OF THE INVENTION

Provided herein are compositions, kits, and methods for the identification of depressive disorders. In particular, provided herein are compositions, kits, and methods for the detection or diagnosis of major depressive disorder.

Levels (e.g., transcript levels (e.g., blood transcript levels, etc.), protein levels, etc.) differ between subjects with a depressive disorder (e.g., MDD) and control subjects (e.g., subject not suffering from a depressive disorder (e.g., MDD)) for the biomarkers ADCY3, DGKA, FAM46A, IGSF4A/CADM1, KIAA1539, MARCKS, PSME1, RAPH1, and/or TLR7. In some embodiments, the provided herein are methods for assessing depressive disorders in a subject, comprising: (a) characterizing (e.g., measuring) in a sample from the subject the levels of gene expression of one or more genes selected from the genes selected from ADCY3, DGKA, FAM46A, IGSF4A/CADM1, KIAA1539, MARCKS, PSME1, RAPH1, and TLR7; and (b) identifying risk of depressive disorders in the subject based on the levels of gene expression and/or protein expression. In some embodiments, step (b) comprises diagnosing the subject as suffering from a depressive disorder (e.g., MDD). In some embodiments, step (a) comprises detecting KIAA1539 and/or RAPH1.

In some embodiments, the subject is a human subject. In some embodiments, the subject is an adult. In some embodiments, the human subject is suspected of suffering from a depressive disorder. In some embodiments, the subject is suspected of suffering from MDD. In some embodiments, assessing depressive disorders comprises: detecting, quantifying, diagnosing, indicating, or determining the presence, risk, severity, and/or type of depressive disorder.

In some embodiments, characterizing the levels of gene expression comprises detecting the amount of RNA (e.g., mRNA). In some embodiments, detecting the amount of RNA (e.g., mRNA) comprises exposing a sample to nucleic acid primers complementary to the mRNA. In some embodiments, detecting the amount of RNA (e.g., mRNA) comprises exposing a sample to nucleic acid probes complementary to the RNA (e.g., mRNA). In some embodiments, nucleic acid probes are linked to a solid surface. In some embodiments, nucleic acid probes are free in solution. In some embodiments, detecting the amount of RNA (e.g., mRNA) in a sample comprises use of a detection technique selected from the group consisting of microarray analysis, reverse transcriptase PCR, quantitative reverse transcriptase PCR, and hybridization analysis. In some embodiments, synthetic (e.g., non-natural) cDNA is generated from biomarker RNA (e.g., mRNA).

In some embodiments, characterizing the levels of gene expression comprises detecting the amount of protein (e.g. in a sample). In some embodiments, detecting the amount of protein comprises using antibodies, antibody fragments, aptamers, or other protein binding agents.

In some embodiments, the present invention provides prescribing and/or administering an appropriate method of treatment for depression based on the findings on the findings in of a diagnostic method described herein (e.g., presence of diagnostic levels of one or more biomarkers). Such treatments, or prescription for treatment, may comprise psychoanalysis or psychotherapy (e.g., cognitive behavioral therapy, etc.), pharmaceutical treatment (e.g., anti-depressives, anti-anxiety, etc.), hospitalization or residential treatment, electroconvulsive therapy (ECT), transcranial magnetic stimulation (TMS), or combinations thereof. In some embodiments, methods further comprise a step of retesting said subject for depression (e.g., following treatment).

In some embodiments, methods comprise subsequent re-testing for biomarkers (e.g., following treatment, after a particular time period (e.g., 1 week, 1 month, 6 months, 1 year, 2 years, etc.), etc.).

In some embodiments, provided herein are kits, reagent mixtures, and/or panels comprising reagents for detecting one or more biomarkers described herein, alone or in combination with other biomarkers. In some embodiments, kits, reagent mixtures, and/or panels comprise reagents for detecting two or more biomarkers. In some embodiments, kits reagent mixtures, and/or panels comprise reagents for detecting two or more biomarkers from Tables 1 and 2 (e.g., 2, 3, 4, 5, 6, 7, 8, 9, 10 . . . 15 . . . 20 . . . 30 . . . 40 . . .

50 . . . 100, or more). In some embodiments, kits, reagent mixtures, and/or panels comprise reagents for detecting fewer than 1000 biomarkers (e.g., <500, <100, <50, <20, <10). In some embodiments, the genes comprise a variant of one or more of the genes described herein (e.g. >50% identity, >60% identity, >70% identity, >80% identity, >90% identity, >95% identity, >98% identity, >99% identity). In some embodiments, reagents are provided for detecting one or more of ADCY3, DGKA, FAM46A, IGSF4A/CADM1, KIAA1539, MARCKS, PSME1, RAPH1, and TLR7. In some embodiments, reagents are provided for detecting RAPH1, and optionally one or more additional markers selected from ADCY3, DGKA, FAM46A, IGSF4A/CADM1, KIAA1539, MARCKS, PSME1, and TLR7, and optionally one or more other markers (e.g., of depression, of another condition, etc.). In some embodiments, reagents are provided for detecting one or more of ADCY3, DGKA, FAM46A, IGSF4A/CADM1, KIAA1539, MARCKS, PSME1, RAPH1, and TLR7. In some embodiments, reagents are provided for detecting KIAA1539, and optionally one or more additional markers selected from ADCY3, DGKA, FAM46A, IGSF4A/CADM1, RAPH1, MARCKS, PSME1, and TLR7, and optionally one or more other markers (e.g., of depression, of another condition, etc.). In some embodiments, reagents are provided for detecting one or more of ADCY3, DGKA, FAM46A, IGSF4A/CADM1, KIAA1539, MARCKS, PSME1, RAPH1, and TLR7. In some embodiments, reagents are provided for detecting RAPH1 and KIAA1539, and optionally one or more additional markers selected from ADCY3, DGKA, FAM46A, IGSF4A/CADM1, MARCKS, PSME1, and TLR7, and optionally one or more other markers (e.g., of depression, of another condition, etc.).

In some embodiments, provided herein are methods comprising one or more (e.g., all) of the steps of: (a) obtaining a biological sample (e.g., blood, urine, etc.,) from a subject; (b) having the sample tested for the level of one or more of ADCY3, DGKA, FAM46A, IGSF4A/CADM1, KIAA1539, MARCKS, PSME1, RAPH1, and TLR7; (c) identifying the subject as suffering from depression (e.g., MDD) or having an increased risk of suffering from depression if the level of one or more of ADCY3, DGKA, FAM46A, IGSF4A/CADM1, KIAA1539, MARCKS, PSME1, RAPH1, and TLR7 is outside a threshold range or beyond (e.g., higher or lower than) a threshold value. In some embodiments, having the sample tested comprises performing an assay to determine biomarker levels. In some embodiments, having the sample tested comprises sending or delivering the sample (or a processed version thereof) to a facility to be assayed to determine biomarker levels. In other embodiments, having the sample tested comprises performing an assay to determine biomarker levels.

In some embodiments, provided herein are methods comprising one or more (e.g., all) of the steps of: (a) receiving a biological sample (e.g., blood, urine, etc,) taken from a subject (e.g., taken by the subject, taken by a clinician, etc.); (b) testing the sample for the level of one or more of ADCY3, DGKA, FAM46A, IGSF4A/CADM1, KIAA1539, MARCKS, PSME1, RAPH1, and TLR7; (c) identifying the subject as suffering from depression (e.g., MDD) or having an increased risk of suffering from depression if the level of one or more of ADCY3, DGKA, FAM46A, IGSF4A/CADM1, KIAA1539, MARCKS, PSME1, RAPH1, and TLR7 is outside a threshold range or beyond (e.g., higher or lower than) a threshold value. In some embodiments, step (c) comprising generating a risk profile or a signature based on the compilation of a plurality of tested markers. In some embodiments, step (d) comprising generating a report and/or sending a report based on one or more of steps (b)-(d).

In some embodiments, a method comprises: (a) quantitating the levels of a plurality (e.g., 2, 3, 4, 5, 6, 7, 8, 9, 10, or more) of biomarkers (e.g., RAPH1, KIAA1539, etc.) in a sample that are indicative of the likelihood that a subject suffers from or will develop depression; and (b) generating a depression profile (or depression risk profile) based on the levels of a plurality of biomarkers. In some embodiments, a computer-based algorithm is used to convert the levels of a plurality of biomarkers into the risk profile. In some embodiments, the levels of the biomarkers, or the biomarkers themselves, are differentially weighted to determine the profile. In some embodiments, the profile is a quantitative value or a qualitative risk. In some embodiments, methods further comprise: (c) generating a report that (i) provides the profile generated in step (b), (ii) indicates the likelihood of the subject developing depression, or (iii) indicates that likelihood that the subject suffers from depression.

In some embodiments, provided herein are methods comprising: (a) identifying a subject as suffering from depression based on the level of one or more genes selected from ADCY3, DGKA, FAM46A, IGSF4A/CADM1, KIAA1539, MARCKS, PSME1, RAPH1, and TLR7, or proteins encoded thereby; and (b) administering a therapy (or prescribing a therapy) for depression to the subject. In some embodiments, identifying a subject as suffering from depression further comprises psychological evaluation of the subject. In some embodiments, administering treatment comprises psychoanalysis, psychotherapy, and/or psychological therapy of the subject. In some embodiments, administering treatment comprises cognitive behavioral therapy. In some embodiments, administering treatment comprises administering, providing, or prescribing one or more pharmaceutical agents to the subject. In some embodiments, pharmaceutical agents comprise anti-depressant medication and/or anti-anxiety medication.

In some embodiments, detection of biomarkers (e.g., expression products) comprises generation of cDNA (e.g., by reverse transcription) from the mRNA (e.g., biomarker mRNA) in a sample, and detecting the cDNA. In some embodiments, cDNA is further amplified prior to detection (e.g., by qPCR). In some embodiments, reverse-transcriptase PCR (RT-PCR) is used to detect the expression of RNA. In RT-PCR, RNA is enzymatically converted to complementary DNA or "cDNA" using a reverse transcriptase enzyme. The cDNA may be detected or used as a template for a PCR reaction. PCR products can be detected by any suitable method, including but not limited to, gel electrophoresis and staining with a DNA specific stain or hybridization to a labeled probe. In some embodiments, the quantitative reverse transcriptase PCR with standardized mixtures of competitive templates method described in U.S. Pat. Nos. 5,639,606, 5,643,765, and 5,876,978 (each of which is herein incorporated by reference) is utilized.

In some embodiments, reagents are provided for the detection and/or quantification of biomarker nucleic acid (e.g., mRNA). Suitable reagents include amplification and/or detection reagents, such as primers and/or probes. Primers and probes may be labeled (e.g., fluorescently) or unlabeled, and may by free in solution or immobilized (e.g., on a bead, well, surface, chip, etc.).

In some embodiments, biomarkers (e.g., expression products) are proteins corresponding to the biomarkers of the panel. In some embodiments, detecting the levels of expression products comprises exposing the sample to antibodies (or antibody fragments, or aptamers, etc.) for the proteins corresponding to the biomarkers of the panel. In some embodiments, antibodies are covalently linked to a solid surface. In some embodiments, detecting the levels of expression products comprises exposing the sample to a mass analysis technique (e.g., mass spectrometry).

In some embodiments, reagents are provided for the detection and/or quantification of biomarker proteins. Suitable reagents include primary antibodies (e.g., that bind to the biomarkers), secondary antibodies (e.g., that bind primary antibodies), antibody fragments, aptamers, etc. Protein detection reagents may be labeled (e.g., fluorescently) or unlabeled, and may by free in solution or immobilized (e.g., on a bead, well, surface, chip, etc.).

In some embodiments, provided herein are methods of treating depression in a subject comprising (a) determining the levels of one or more biomarkers described herein in a biological sample from a subject, said biomarkers being indicative or diagnostic of depression (e.g., MDD), and (b) administering a therapy for depression. In some embodiments, therapy is selected from the group consisting of psychoanalysis, psychotherapy, pharmaceutical treatment, electroshock therapy, etc.

In some embodiments, biomarkers indicative or diagnostic of depression (e.g., MDD) are proteins or protein subunits, the concentration of which in a biological sample (e.g., blood, urine, tissues, etc.) are altered when compared to a control. In some embodiments, protein detection and/or quantification reagents are provided. In embodiments in which a biomarker is a protein, polypeptide and/or peptide, detection and/or quantification reagents may comprise antibodies or antibody-like reagents, aptamers, etc. that bind (e.g., specifically) to the biomarker(s). In such embodiments, detection and/or quantification may be achieved by, for example, an immunoassay, Western blot, enzyme-linked immunosorbent assay (ELISA), radioimmunoassay (MA), fluorimetric assay, or other suitable assays known in the field.

In some embodiments, biomarkers indicative or diagnostic of depression are RNAs (e.g., mRNA) encoding proteins or subunits thereof, the concentration or level of expression of which (e.g., in a biological sample (e.g., blood, urine, tissues, etc.)) are altered when compared to a control. In embodiments in which a biomarker is an RNA (e.g., mRNA), detection and/or quantification reagents may comprise primers (e.g., for amplification, reverse transcription, etc.) or probes (e.g., detectably-labeled (e.g., optically-labeled, fluorescently labeled, etc.) oligonucleotides) that bind (e.g., specifically) to the biomarker. In such embodiments, detection and/or quantification may be achieved by, for example, RT-PCR, qPCR, Northern blot analysis, an enzymatic cleavage assay (e.g., INVADER, Hologic, Inc.; See e.g., U.S. Pat. Nos. 5,846,717, 6,090,543; 6,001,567; 5,985,557; and 5,994,069; each of which is herein incorporated by reference), a hybridization assay (e.g., TaqMan assay (Life Technologies; See e.g., U.S. Pat. Nos. 5,962,233 and 5,538,848, each of which is herein incorporated by reference), etc.

DESCRIPTION OF THE DRAWINGS

FIG. 1 shows scatter plots of delta CT values for each transcript measured at baseline in MDD subjects and their matched controls. A reference line is presented along the diagonal, hence if data is below the line, control levels are higher (concentration=2-delta CT) than MDD levels, or if the points trend above the line, control levels are lower. Bolded transcript names differed significantly between MDD and control subjects as indicated in Table 3.

DEFINITIONS

As used herein, the term "subject" refers to any animal (e.g., a mammal), including, but not limited to, humans, non-human primates, rodents, and the like. Typically, the terms "subject" and "patient" are used interchangeably herein in reference to a human subject.

As used herein, the term "adult" refers to an individual who has attained physical and/or psychological maturity (e.g., >16 years old, >18 years old, >20 years old, etc.).

As used herein, the terms "subject suspected of having depression" or "subject suspected of having MDD" refer to a subject that presents one or more symptoms indicative of depression or MDD, has one or more risk factors for depression or MDD, or is being screened for depression or MDD (e.g., during a routine physical). A subject suspected of having depression or MDD may not have been tested for depression or MDD (e.g., by the methods described herein or by other methods), or may not have had a recent test, which indicated the subject suffers from depression or MDD. However, a "subject suspected of having depression or MDD" encompasses an individual who has received a preliminary diagnosis but for whom a confirmatory test has not been done. A "subject suspected of having depression or MDD" is sometimes diagnosed with depression or MDD and is sometimes found to not have depression or MDD.

As used herein, the terms "subject diagnosed with depression" and "subject diagnosed with MDD" refers to a subject who has been tested and found to have depression or MDD. Subject may be diagnosed using any suitable method, including those described herein.

As used herein, the terms "subject suffering from depression" and "subject suffering with MDD" refers to a subject who has depression or MDD and exhibits one or more symptoms thereof (whether or not symptoms are apparent). A subject suffering from depression or MDD may or may not have received a diagnosis, and may or may not be aware of the condition.

As used herein, the term "subject at risk for depression or MDD" refers to a subject with one or more risk factors for developing depression or MDD (e.g., genetics).

As used herein, the term "providing a prognosis" refers to providing information regarding the impact of depression or MDD on a subject's future health.

As used herein, the term "sample" is used in its broadest sense. In one sense, it is meant to include a specimen or culture obtained from any source. Biological samples may be obtained from animals (including humans) and encompass fluids, solids, tissues, and gases. Biological samples include urine, saliva, tissues, lacrimal fluid, blood, and blood products, such as plasma, serum and the like.

As used herein, the term "reagent(s) capable of specifically detecting biomarker expression" refers to reagents used to detect the expression of biomarkers (e.g., RAPH1, KIAA1539, etc. (e.g., in the blood (e.g., above/below a threshold))). Examples of suitable reagents include but are not limited to, nucleic acid probes capable of specifically hybridizing to mRNA or cDNA, and antibodies (e.g., monoclonal antibodies).

As used here, the term "antibody" includes monoclonal antibodies (including full length monoclonal antibodies), polyclonal antibodies, multispecific antibodies (e.g., bispecific antibodies), humanized antibodies, and antibody fragments so long as they exhibit the desired biological activity.

Antibodies can be conjugated to other molecules (e.g., toxins). As used herein, the term "antibody fragments" refers to a portion of an intact antibody. Examples of antibody fragments include, but are not limited to, linear antibodies; single-chain antibody molecules; Fc or Fc' peptides, Fab and Fab fragments, and multispecific antibodies formed from antibody fragments.

The terms "specific binding" or "specifically binding" when used in reference to the interaction of capture or detection reagent (e.g., antibody, probe, etc.) and a target or biomarker (e.g., protein, DNA, RNA, etc.) means that the interaction is dependent upon the presence of a particular structure (i.e., the antigenic determinant or epitope; the nucleic acid sequence) and that targets or markers lacking such structures are not bound to a substantial degree by the reagent.

As used herein, the terms "non-specific binding" and "background binding" when used in reference to the interaction capture or detection reagent (e.g., antibody probe etc.) and a target or biomarker (e.g., protein, DNA, RNA, etc.) refer to an interaction that is not dependent on the presence of a particular structure or sequence.

As used herein, "a reagent that specifically detects expression levels" refers to reagents used to detect the expression of one or more genes (e.g., including but not limited to, the biomarkers herein). Examples of suitable reagents include but are not limited to, nucleic acid probes capable of specifically hybridizing to the gene of interest, aptamers, PCR primers capable of specifically amplifying the gene of interest, and antibodies capable of specifically binding to proteins expressed by the gene of interest.

As used herein, the term "nucleic acid detection assay" refers to any method of determining the nucleotide composition of a nucleic acid of interest. Nucleic acid detection assay include but are not limited to, DNA sequencing methods, probe hybridization methods, enzyme mismatch cleavage methods (e.g., Variagenics, U.S. Pat. Nos. 6,110,684, 5,958,692, 5,851,770, herein incorporated by reference in their entireties); polymerase chain reaction; branched hybridization methods (e.g., Chiron, U.S. Pat. Nos. 5,849,481, 5,710,264, 5,124,246, and 5,624,802, herein incorporated by reference in their entireties); rolling circle replication (e.g., U.S. Pat. Nos. 6,210,884, 6,183,960 and 6,235,502, herein incorporated by reference in their entireties); NASBA (e.g., U.S. Pat. No. 5,409,818, herein incorporated by reference in its entirety); molecular beacon technology (e.g., U.S. Pat. No. 6,150,097, herein incorporated by reference in its entirety); E-sensor technology (Motorola, U.S. Pat. Nos. 6,248,229, 6,221,583, 6,013,170, and 6,063,573, herein incorporated by reference in their entireties); cycling probe technology (e.g., U.S. Pat. Nos. 5,403,711, 5,011,769, and 5,660,988, herein incorporated by reference in their entireties); Dade Behring signal amplification methods (e.g., U.S. Pat. Nos. 6,121,001, 6,110,677, 5,914,230, 5,882,867, and 5,792,614, herein incorporated by reference in their entireties); ligase chain reaction (e.g., Barnay Proc. Natl. Acad. Sci USA 88, 189-93 (1991)); and sandwich hybridization methods (e.g., U.S. Pat. No. 5,288,609, herein incorporated by reference in its entirety).

The term "primer" refers to an oligonucleotide, whether occurring naturally as in a purified restriction digest or produced synthetically, that is capable of acting as a point of initiation of synthesis when placed under conditions in which synthesis of a primer extension product that is complementary to a nucleic acid strand is induced, (e.g., in the presence of nucleotides and an inducing agent such as a DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer, and the use of the method.

The term "probe" refers to an oligonucleotide (e.g., a sequence of nucleotides), whether occurring naturally as in a purified restriction digest or produced synthetically, recombinantly, or by PCR amplification, that is capable of hybridizing to another oligonucleotide of interest. A probe may be single-stranded or double-stranded. Probes are useful in the detection, identification, and isolation of particular gene sequences (e.g., a "capture probe"). It is contemplated that any probe used in the present invention may, in some embodiments, be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, a "diagnostic" test application includes the detection or identification of a disease state or condition of a subject, determining the likelihood that a subject will contract a given disease or condition, determining the likelihood that a subject with a disease or condition will respond to therapy, determining the prognosis of a subject with a disease or condition (or its likely progression or regression), and determining the effect of a treatment on a subject with a disease or condition.

DETAILED DESCRIPTION OF THE INVENTION

Provided herein are compositions, kits, and methods for the identification of depressive disorders. In particular, provided herein are compositions, kits, and methods for the detection or diagnosis of major depressive disorder.

Major depressive disorder (MDD) is a complex psychiatric disease, affecting 6.7% of the U.S. adult population in a year (Kessler et al. Arch Gen Psychiatry 2005; 62: 593-602.; herein incorporated by reference in its entirety), with a steadily increasing prevalence (Hidaka. J Affect Disord 2012; 140: 205-14.; Lepine & Briley. Neuropsychiatr Dis Treat 2011; 7: 3-7.; herein incorporated by reference in their entireties). The World Health Organization has determined that depressive disorders are the leading cause of disability worldwide (Ferrari et al. PLoS Med 2013; 10: e1001547.; herein incorporated by reference in its entirety). The recurrent and chronic forms of depression account for the bulk of the high burden associated with the disorder (Hardeveld et al. Acta psychiatrica Scandinavica 2010; 122: 184-91.; herein incorporated by reference in its entirety). Successful treatment of depression relies first upon accurate diagnosis. Currently, depression is diagnosed based on the patients' self-report of their symptoms, and the evaluation of the structured psychiatric interview(s) with the patient by a psychiatrist, psychologist or primary care physician. The severity of self-reported and clinician rated depression symptoms are sometimes in conflict as depressed patients frequently underreport depression symptoms or inadequately characterize them (Carter et al. J Affect Disord 2010; 124: 202-6.; herein incorporated by reference in its entirety). Similarly, there is no perfect harmony between the different depression scoring systems (Riedel et al. J Psychiatr Res 2010; 44: 1063-8.; herein incorporated by reference in its entirety). There are no reliable objective biological diagnostic tests for major depression either (Belmaker & Agam. The New England Journal of Medicine 2008; 358: 55-68.; herein incorporated by reference in its entirety). The diagnostic delay is 2-40 months and the longer this period is the more difficult it is to treat depression (Altamura et al. Int Clin Psychopharmacol 2010; 25: 172-9.; Huerta-Ramirez et al. J Affect Disord 2013; 150: 1247-50.; herein incorporated by reference in their entireties). Most depression is treated in primary care: it is estimated that 12.5% of primary care patients have had MDD in any given year, but only 47% of those cases are recognized clinically (Pence et al. Curr Psychiatry Rep 2012; 14: 328-35.; herein incorporated by reference in its entirety).

Provided herein are objective diagnostic tools that, for example, increase accuracy of diagnosis for depressive disorders (e.g., major depressive disorder (MDD)), and promote individualized therapy. Experiments were conducted during development of embodiments described herein to identify blood-based biomarkers (e.g., a biomarker panel). A group of adult primary care patients with MDD and age, gender and race-matched non-depressed (ND) controls were studied. Blood transcript levels of nine markers, of ADCY3, DGKA, FAM46A, IGSF4A/CADM1, KIAA1539, MARCKS, PSME1, RAPH1 and TLR7, differed significantly between participants with MDD (N=32) and ND controls (N=32) at baseline (q<0.05). Thus, blood levels of transcript panel, or a portion of the biomarkers therein (e.g., RAPH1 and/or KIAA1539), discriminated between depressed and non-depressed subjects.

In some embodiments, a subject to be tested by the methods and reagents described herein exhibits one or more symptoms of depression and/or has one or more risk factors for depression. Symptoms of depression include, for example: feelings of sadness, emptiness or unhappiness; angry outbursts, irritability or frustration, even over small matters; loss of interest or pleasure in normal activities, such as sex; sleep disturbances, including insomnia or sleeping too much; tiredness and lack of energy, so that even small tasks take extra effort; changes in appetite—often reduced appetite and weight loss, but increased cravings for food and weight gain in some people; anxiety, agitation or restlessness—for example, excessive worrying, pacing, hand-wringing or an inability to sit still; slowed thinking, speaking or body movements; feelings of worthlessness or guilt, fixating on past failures or blaming yourself for things that are not your responsibility; trouble thinking, concentrating, making decisions and remembering things; frequent thoughts of death, suicidal thoughts, suicide attempts or suicide; Unexplained physical problems, such as back pain or headaches; etc. Risk factors of depression include, for example: depression that started when you were a teen or child; history of anxiety disorder, borderline personality disorder or post-traumatic stress disorder; abuse of alcohol or illegal drugs; certain personality traits, such as having low self-esteem and being overly dependent, self-critical or pessimistic; serious or chronic illness, such as cancer, diabetes or heart disease; certain medications, such as some high blood pressure medications or sleeping pills (talk to your doctor before stopping any medication); traumatic or stressful events, such as physical or sexual abuse, the loss of a loved one, a difficult relationship or financial problems; blood relatives with a history of depression, bipolar disorder, alcoholism or suicide; etc. In some embodiments, prior to, concurrent with, and/or following testing a subject for the biomarkers of vulnerability to recurrent depression described herein, a subject is evaluated for symptoms and/or risk factors.

The level of biomarker(s) present in a sample may be assessed on an absolute basis or a relative basis. When assessed on a relative basis, comparison may be made to controls including but not limited to a historical sample from the same patient (e.g., serial samples, longitudinal samples); level(s) found in a patient or population of patients absent of disease or disorder; a threshold value; an acceptable range; etc.

In some embodiments, provided herein are DNA-, RNA- and protein-based diagnostic methods that either directly or indirectly detect the biomarkers described herein. The present invention also provides compositions, reagents, and kits for such diagnostic purposes. The diagnostic methods described herein may be qualitative or quantitative. Quantitative diagnostic methods may be used, for example, to compare a detected biomarker level to a cutoff or threshold level. Where applicable, qualitative or quantitative diagnostic methods may also include amplification of target, signal or intermediary.

In some embodiments, biomarkers are detected at the nucleic acid (e.g., RNA) level. For example, the amount of biomarker RNA (e.g., mRNA) present in a sample is determined (e.g., to determine the level of biomarker expression). Biomarker nucleic acid (e.g., RNA, amplified cDNA, etc.) may be detected/quantified using a variety of nucleic acid techniques known to those of ordinary skill in the art, including but not limited to nucleic acid sequencing, nucleic acid hybridization, and nucleic acid amplification.

A variety of biological assays may be used to assess expression levels of depression markers. For example, in some embodiments, a microarray is used. Different kinds of biological assays are called microarrays including, but not limited to: DNA microarrays (e.g., cDNA microarrays and oligonucleotide microarrays); protein microarrays; tissue microarrays; transfection or cell microarrays; chemical compound microarrays; and, antibody microarrays. A DNA microarray, commonly known as gene chip, DNA chip, or biochip, is typically a collection of microscopic DNA spots attached to a solid surface (e.g., glass, plastic or silicon chip) forming an array for the purpose of expression profiling or monitoring expression levels for thousands of genes simultaneously. The affixed DNA segments are known as probes, thousands of which can be used in a single DNA microarray. Microarrays can be used to identify disease genes by comparing gene expression in disease and normal cells. Microarrays can be fabricated using a variety of technologies, including but not limiting: printing with fine-pointed pins onto glass slides; photolithography using pre-made masks; photolithography using dynamic micromirror devices; ink-jet printing; or, electrochemistry on microelectrode arrays.

Southern and Northern blotting is used to detect specific DNA or RNA sequences, respectively. DNA or RNA extracted from a sample is fragmented, electrophoretically separated on a matrix gel, and transferred to a membrane filter. The filter bound DNA or RNA is subject to hybridization with a labeled probe complementary to the sequence of interest. Hybridized probe bound to the filter is detected. A variant of the procedure is the reverse Northern blot, in which the substrate nucleic acid that is affixed to the membrane is a collection of isolated DNA fragments and the probe is RNA extracted from a tissue and labeled.

Genomic DNA and mRNA may be amplified prior to or simultaneous with detection. Illustrative non-limiting examples of nucleic acid amplification techniques include, but are not limited to, polymerase chain reaction (PCR), reverse transcription polymerase chain reaction (RT-PCR), transcription-mediated amplification (TMA), ligase chain reaction (LCR), strand displacement amplification (SDA) and nucleic acid sequence based amplification (NASBA). Those of ordinary skill in the art will recognize that certain amplification techniques (e.g., PCR) require that RNA be reversed transcribed to DNA prior to amplification (e.g., RT-PCR), whereas other amplification techniques directly amplify RNA (e.g., TMA and NASBA).

The polymerase chain reaction, commonly referred to as PCR, uses multiple cycles of denaturation, annealing of primer pairs to opposite strands, and primer extension to exponentially increase copy numbers of a target nucleic acid sequence. In a variation called RT-PCR, reverse transcriptase (RT) is used to make a complementary DNA (cDNA) from mRNA, and the cDNA is then amplified by PCR to produce multiple copies of DNA.

Transcription mediated amplification (U.S. Pat. Nos. 5,480,784 and 5,399,491, each of which is herein incorporated by reference in its entirety), commonly referred to as TMA, synthesizes multiple copies of a target nucleic acid sequence autocatalytically under conditions of substantially constant temperature, ionic strength, and pH in which multiple RNA copies of the target sequence autocatalytically generate additional copies. See, e.g., U.S. Pat. Nos. 5,399, 491 and 5,824,518, each of which is herein incorporated by reference in its entirety. In a variation described in U.S. Publ. No. 20060046265 (herein incorporated by reference in its entirety), TMA optionally incorporates the use of blocking moieties, terminating moieties, and other modifying moieties to improve TMA process sensitivity and accuracy.

The ligase chain reaction (Weiss, R., *Science* 254: 1292 (1991), herein incorporated by reference in its entirety), commonly referred to as LCR, uses two sets of complementary DNA oligonucleotides that hybridize to adjacent regions of the target nucleic acid. The DNA oligonucleotides are covalently linked by a DNA ligase in repeated cycles of thermal denaturation, hybridization and ligation to produce a detectable double-stranded ligated oligonucleotide product.

Strand displacement amplification (Walker, G. et al., *Proc. Natl. Acad. Sci. USA* 89: 392-396 (1992); U.S. Pat. Nos. 5,270,184 and 5,455,166, each of which is herein incorporated by reference in its entirety), commonly referred to as SDA, uses cycles of annealing pairs of primer sequences to opposite strands of a target sequence, primer extension in the presence of a dNTPaS to produce a duplex hemiphosphorothioated primer extension product, endonuclease-mediated nicking of a hemimodified restriction endonuclease recognition site, and polymerase-mediated primer extension from the 3' end of the nick to displace an existing strand and produce a strand for the next round of primer annealing, nicking and strand displacement, resulting in geometric amplification of product. Thermophilic SDA (tSDA) uses thermophilic endonucleases and polymerases at higher temperatures in essentially the same method (EP Pat. No. 0 684 315).

Other amplification methods include, for example: nucleic acid sequence based amplification (U.S. Pat. No. 5,130,238, herein incorporated by reference in its entirety), commonly referred to as NASBA; one that uses an RNA replicase to amplify the probe molecule itself (Lizardi et al., *BioTechnol.* 6: 1197 (1988), herein incorporated by reference in its entirety), commonly referred to as Qβ replicase; a transcription based amplification method (Kwoh et al., *Proc. Natl. Acad. Sci. USA* 86:1173 (1989)); and, self-sustained sequence replication (Guatelli et al., *Proc. Natl. Acad. Sci. USA* 87: 1874 (1990), each of which is herein incorporated by reference in its entirety). For further discussion of known amplification methods see Persing, David H., "In Vitro Nucleic Acid Amplification Techniques" in *Diagnostic Medical Microbiology: Principles and Applications* (Persing et al., Eds.), pp. 51-87 (American Society for Microbiology, Washington, D.C. (1993)).

Non-amplified or amplified nucleic acids can be detected by any conventional means. For example, in some embodiments, nucleic acids are detected by hybridization with a detectably labeled probe and measurement of the resulting hybrids. Illustrative non-limiting examples of detection methods are described below.

One illustrative detection method, the Hybridization Protection Assay (HPA) involves hybridizing a chemiluminescent oligonucleotide probe (e.g., an acridinium ester-labeled (AE) probe) to the target sequence, selectively hydrolyzing the chemiluminescent label present on unhybridized probe, and measuring the chemiluminescence produced from the remaining probe in a luminometer. See, e.g., U.S. Pat. No. 5,283,174 and Norman C. Nelson et al., Nonisotopic Probing, Blotting, and Sequencing, ch. 17 (Larry J. Kricka ed., 2d ed. 1995, each of which is herein incorporated by reference in its entirety).

Another illustrative detection method provides for quantitative evaluation of the amplification process in real-time. Evaluation of an amplification process in "real-time" involves determining the amount of amplicon in the reaction mixture either continuously or periodically during the amplification reaction, and using the determined values to calculate the amount of target sequence initially present in the sample. A variety of methods for determining the amount of initial target sequence present in a sample based on real-time amplification are well known in the art. These include methods disclosed in U.S. Pat. Nos. 6,303,305 and 6,541, 205, each of which is herein incorporated by reference in its entirety. Another method for determining the quantity of target sequence initially present in a sample, but which is not based on a real-time amplification, is disclosed in U.S. Pat. No. 5,710,029, herein incorporated by reference in its entirety.

Amplification products may be detected in real-time through the use of various self-hybridizing probes, most of which have a stem-loop structure. Such self-hybridizing probes are labeled so that they emit differently detectable signals, depending on whether the probes are in a self-hybridized state or an altered state through hybridization to a target sequence. By way of non-limiting example, "molecular torches" are a type of self-hybridizing probe that includes distinct regions of self-complementarity (referred to as "the target binding domain" and "the target closing domain") which are connected by a joining region (e.g., non-nucleotide linker) and which hybridize to each other under predetermined hybridization assay conditions. In a preferred embodiment, molecular torches contain single-stranded base regions in the target binding domain that are from 1 to about 20 bases in length and are accessible for hybridization to a target sequence present in an amplification reaction under strand displacement conditions. Under strand displacement conditions, hybridization of the two complementary regions, which may be fully or partially complementary, of the molecular torch is favored, except in the presence of the target sequence, which will bind to the single-stranded region present in the target binding domain and displace all or a portion of the target closing domain.

The target binding domain and the target closing domain of a molecular torch include a detectable label or a pair of interacting labels (e.g., luminescent/quencher) positioned so that a different signal is produced when the molecular torch is self-hybridized than when the molecular torch is hybridized to the target sequence, thereby permitting detection of probe:target duplexes in a test sample in the presence of unhybridized molecular torches. Molecular torches and a variety of types of interacting label pairs are disclosed in U.S. Pat. No. 6,534,274, herein incorporated by reference in its entirety.

Another example of a detection probe having self-complementarity is a "molecular beacon." Molecular beacons include nucleic acid molecules having a target complementary sequence, an affinity pair (or nucleic acid arms) holding the probe in a closed conformation in the absence of a target sequence present in an amplification reaction, and a label pair that interacts when the probe is in a closed conformation. Hybridization of the target sequence and the target complementary sequence separates the members of the affinity pair, thereby shifting the probe to an open conformation. The shift to the open conformation is detectable due to reduced interaction of the label pair, which may be, for example, a fluorophore and a quencher (e.g., DABCYL and EDANS). Molecular beacons are disclosed in U.S. Pat. Nos. 5,925,517 and 6,150,097, herein incorporated by reference in its entirety.

Other self-hybridizing probes are well known to those of ordinary skill in the art. By way of non-limiting example, probe binding pairs having interacting labels, such as those disclosed in U.S. Pat. No. 5,928,862 (herein incorporated by reference in its entirety) might be adapted for use in the present invention. Probe systems used to detect single nucleotide polymorphisms (SNPs) might also be utilized in the present invention. Additional detection systems include "molecular switches," as disclosed in U.S. Publ. No. 20050042638, herein incorporated by reference in its entirety. Other probes, such as those comprising intercalating dyes and/or fluorochromes, are also useful for detection of amplification products in the present invention. See, e.g., U.S. Pat. No. 5,814,447 (herein incorporated by reference in its entirety).

In some embodiments, quantitative PCR (qPCR) is utilized, e.g., using SYBR Green dye on an Applied Biosystems 7300 Real Time PCR system essentially as described (Chinnaiyan et al., Cancer Res 65, 3328 (2005); Rubin et al., Cancer Res 64, 3814 (2004); herein incorporated by reference in its entirety).

In some embodiments, nucleic acid from a sample is sequenced (e.g., in order to detect biomarkers). Nucleic acid molecules may be sequence analyzed by any number of techniques. The analysis may identify the sequence of all or a part of a nucleic acid. Illustrative non-limiting examples of nucleic acid sequencing techniques include, but are not limited to, chain terminator (Sanger) sequencing and dye terminator sequencing, as well as "next generation" sequencing techniques. Those of ordinary skill in the art will recognize that because RNA is less stable in the cell and more prone to nuclease attack, experimentally RNA is usually, although not necessarily, reverse transcribed to DNA before sequencing.

A number of DNA sequencing techniques are known in the art, including fluorescence-based sequencing methodologies (See, e.g., Birren et al., Genome Analysis: Analyzing DNA, 1, Cold Spring Harbor, N.Y.; herein incorporated by reference in its entirety). In some embodiments, automated sequencing techniques understood in that art are utilized. In some embodiments, the systems, devices, and methods employ parallel sequencing of partitioned amplicons (PCT Publication No: WO2006084132 to Kevin McKernan et al., herein incorporated by reference in its entirety). In some embodiments, DNA sequencing is achieved by parallel oligonucleotide extension (See, e.g., U.S. Pat. No. 5,750,341 to Macevicz et al., and U.S. Pat. No. 6,306,597 to Macevicz et al., both of which are herein incorporated by reference in their entireties). Additional examples of sequencing techniques include the Church polony technology (Mitra et al., 2003, Analytical Biochemistry 320, 55-65; Shendure et al., 2005 Science 309, 1728-1732; U.S. Pat. Nos. 6,432,360, 6,485,944, 6,511,803; herein incorporated by reference in their entireties) the 454 picotiter pyrosequencing technology (Margulies et al., 2005 Nature 437, 376-380; US 20050130173; herein incorporated by reference in their entireties), the Solexa single base addition technology (Bennett et al., 2005, Pharmacogenomics, 6, 373-382; U.S. Pat. Nos. 6,787,308; 6,833,246; herein incorporated by reference in their entireties), the Lynx massively parallel signature sequencing technology (Brenner et al. (2000). Nat. Biotechnol. 18:630-634; U.S. Pat. Nos. 5,695,934; 5,714,330; herein incorporated by reference in their entireties) and the Adessi PCR colony technology (Adessi et al. (2000). Nucleic Acid Res. 28, E87; WO 00018957; herein incorporated by reference in its entirety).

A set of methods referred to as "next-generation sequencing" techniques have emerged as alternatives to Sanger and dye-terminator sequencing methods (Voelkerding et al., Clinical Chem., 55: 641-658, 2009; MacLean et al., Nature Rev. Microbiol., 7: 287-296; each herein incorporated by reference in their entirety). Next-generation sequencing (NGS) methods share the common feature of massively parallel, high-throughput strategies, with the goal of lower costs in comparison to older sequencing methods. NGS methods can be broadly divided into those that require template amplification and those that do not. Amplification-requiring methods include pyrosequencing commercialized by Roche as the 454 technology platforms (e.g., GS 20 and GS FLX), the Solexa platform commercialized by Illumina, and the Supported Oligonucleotide Ligation and Detection (SOLiD) platform commercialized by Applied Biosystems. Non-amplification approaches, also known as single-molecule sequencing, are exemplified by the HeliScope platform commercialized by Helicos BioSciences, Pacific Biosciences (PAC BIO RS II) and other platforms commercialized.***

In some embodiments, a sample is processed prior to biomarker detection. For example, nucleic acid and/or proteins may be extracted, isolated, and/or purified from a sample prior to analysis. Various DNA, mRNA, and/or protein extraction techniques are well known to those skilled in the art. Processing may include centrifugation, ultracentrifugation, ethanol precipitation, filtration, fractionation, resuspension, dilution, concentration, etc. In some embodiments, methods and systems provide analysis (e.g., quantification of RNA or protein biomarkers) from raw sample (e.g., biological fluid (e.g., blood, serum, etc.) without or with limited processing.

Methods may comprise steps of homogenizing a sample in a suitable buffer, removal of contaminants and/or assay inhibitors, adding a target capture reagent (e.g., a magnetic bead to which is linked an oligonucleotide complementary to the target), incubated under conditions that promote the association (e.g., by hybridization) of the target with the capture reagent to produce a target:capture reagent complex, incubating the target:capture complex under target-release conditions. In some embodiments, multiple biomarker targets are isolated in each round of isolation by adding multiple target capture reagents (e.g., specific to the desired biomarkers) to the solution. For example, multiple target capture reagents, each comprising an oligonucleotide specific for a different biomarker target can be added to the sample for isolation of multiple targets. It is contemplated that the methods encompass multiple experimental designs that vary both in the number of capture steps and in the number of targets captured in each capture step. In some embodiments, capture reagents are molecules, moieties, substances, or compositions that preferentially (e.g., specifically and selectively) interact with a particular biomarker sought to be isolated, purified, detected, and/or quantified. Any capture reagent having desired binding affinity and/or specificity to the analyte target can be used in the present technology. For example, the capture reagent can be a macromolecule such as a peptide, a protein (e.g., an antibody or receptor), an oligonucleotide, a nucleic acid, (e.g., nucleic acids capable of hybridizing with the target nucleic acids), vitamins, oligosaccharides, carbohydrates, lipids, or small molecules, or a complex thereof. As illustrative and non-limiting examples, an avidin target capture reagent may be used to isolate and purify targets comprising a biotin moiety, an antibody may be used to isolate and purify targets comprising the appropriate antigen or epitope, and an oligonucleotide may be used to isolate and purify a complementary oligonucleotide.

Any nucleic acids, including single-stranded and double-stranded nucleic acids, that are capable of binding, or specifically binding, to the target can be used as the capture reagent. Examples of such nucleic acids include DNA, RNA, aptamers, peptide nucleic acids, and other modifications to the sugar, phosphate, or nucleoside base. Thus, there are many strategies for capturing a target and accordingly many types of capture reagents are known to those in the art.

In addition, target capture reagents comprise a functionality to localize, concentrate, aggregate, etc. the capture reagent and thus provide a way to isolate and purify the target biomarker when captured (e.g., bound, hybridized, etc.) to the capture reagent (e.g., when a target:capture reagent complex is formed). For example, in some embodiments the portion of the target capture reagent that interacts with the target (e.g., the oligonucleotide) is linked to a solid support (e.g., a bead, surface, resin, column, and the like) that allows manipulation by the user on a macroscopic scale. Often, the solid support allows the use of a mechanical means to isolate and purify the target:capture reagent complex from a heterogeneous solution. For example, when linked to a bead, separation is achieved by removing the bead from the heterogeneous solution, e.g., by physical movement. In embodiments in which the bead is magnetic or paramagnetic, a magnetic field is used to achieve physical separation of the capture reagent (and thus the target) from the heterogeneous solution. Magnetic beads used to isolate targets are described in the art, e.g., as described in European Patent Application No. 87309308, incorporated herein in its entirety for all purposes.

In some embodiments, a computer-based analysis program is used to translate the raw data generated by the detection assay (e.g., the presence, absence, or amount of expression a panel of genes) into data of predictive value for a clinician (e.g., a risk score, a qualitative description, etc.). In some embodiments, computer analysis combines the data from numerous biomarkers into a single score or value that is predictive and/or diagnostic for depression. The clinician can access the predictive data using any suitable means.

Thus, in some preferred embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

The present invention contemplates any method capable of receiving, processing, and transmitting the information to and from laboratories conducting the assays, information providers, medical personal, and subjects. For example, in some embodiments of the present invention, a sample (e.g., a biopsy or a blood or serum sample) is obtained from a subject and submitted to a profiling service (e.g., clinical lab at a medical facility, third-party testing service, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a urine sample) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (i.e., expression data), specific for the diagnostic or prognostic information desired for the subject.

In some embodiments, profile data is prepared in a format suitable for interpretation by a treating clinician. For example, rather than providing raw expression data, the prepared format may represent a diagnosis or risk assessment (e.g., likelihood of depression being present) for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, a report is generated (e.g., by a clinician, by a testing center, by a computer or other automated analysis system, etc.). A report may contain test results, diagnoses, and/or treatment recommendations (e.g., psychoanalysis, psychotherapy, pharmaceutical treatment, observation, etc.).

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may chose further intervention or counseling based on the results. In some embodiments, the data is used for research use. For example, the data may be used to further optimize the inclusion or elimination of markers as useful indicators of a particular condition or stage of disease.

In some embodiments, all or a portion of the methods described herein are provided as a service. In some embodiments, a user (e.g., subject (e.g., patient), clinician, researcher, etc.) arranges, contracts, pays, etc. to have a sample (e.g., biological sample (e.g., blood product, etc.), nucleic acid sample, etc.) and/or data (e.g., raw data) analyzed. In some embodiments, a sample is submitted (e.g., in-person, via mail or courier, etc.) and analysis of the sample for specific biomarkers described herein (alone or with other biomarkers is performed by the service (e.g., at a diagnostic testing facility, etc.). In some embodiments, data collected by a user (e.g., a clinician, researcher, etc.) are submitted to a testing facility for analysis. Embodiments described herein include any suitable combination of user-performed (e.g., subject-performed, clinician-performed, etc.) and service-performed steps. In some embodiments, methods described herein comprise of consist of only the steps performed by either the user (e.g., subject, clinician, etc.) of the service (e.g., sample collection, sending a sample, sample analysis, data collection, data analysis, receiving a report, etc.), or the service (e.g., sample collection, receiving a sample, sample analysis, data analysis, generating a report, sending a report, etc.). In some embodiments, any combination of steps may be performed by a user and/or service.

In some embodiments, analysis results are reported (e.g., to a health care professional, to a subject, etc.). In some embodiments, a result is provided on a peripheral, device, or component of an apparatus. For example, sometimes an outcome is provided by a printer or display. In some embodiments, an outcome is reported in the form of a report, and in certain embodiments the report comprises biomarker levels, risk assessment, a compiled score (e.g., based on a plurality of markers), etc. An outcome can be translated into and displayed in a suitable format that facilitates downstream use of the reported information. Non-limiting examples of formats suitable for use for reporting and/or displaying data, characteristics, etc. include text, outline, digital data, a graph, graphs, a picture, a pictograph, a chart, a bar graph, a pie graph, a diagram, a flow chart, a scatter plot, a map, a histogram, a density chart, a function graph, a circuit diagram, a block diagram, a bubble map, a constellation diagram, a contour diagram, a cartogram, spider chart, Venn diagram, nomogram, and the like, and combination of the foregoing.

In some embodiments, generating and reporting results from the raw biomarker data comprises transformation of the data reads into a representation that reflects information not determinable in the absence of the method steps described herein. Converting biomarker levels into useful information allows actions to be taken (e.g., in response to identifying a subject at risk of depression or depressed). As such, the methods provided herein address the problem of identifying depressed subjects or those at risk of depression, a problem that confronts the fields of medicine, public health, public safety, mental health, etc.

In some embodiments, a user or a downstream individual, upon receiving or reviewing a report comprising one or more results determined from the analyses provided herein, will take specific steps or actions in response. For example, a health care professional or qualified individual may provide further testing of a subject. A public health official may take steps provide assistance to the subject. The present invention is not limited by the number of ways or fields in which the technology herein may find use.

The term "receiving a report" as used herein refers to obtaining, by a communication means, a written and/or graphical representation comprising results or outcomes of the biomarker analysis described herein. The report may be generated by a computer or by human data entry, and can be communicated using electronic means (e.g., over the internet, via computer, via fax, from one network location to another location at the same or different physical sites), or by another method of sending or receiving data (e.g., mail service, courier service and the like). In some embodiments, the outcome is transmitted in a suitable medium, including, without limitation, in verbal, document, or file form. The file may be, for example, but not limited to, an auditory file, a computer readable file, a paper file, a laboratory file or a medical record file. A report may be encrypted to prevent unauthorized viewing.

As noted above, in some embodiments, systems and method described herein transform data from one form into another form (e.g., from physical biomarkers in a sample to actual diagnosis, etc.). In some embodiments, the terms "transformed", "transformation", and grammatical derivations or equivalents thereof, refer to an alteration of data from a physical starting material (e.g., nucleic acid or protein in a biological sample, etc.) into a digital representation of the physical starting material (e.g., read data), a representation of the amount of that starting material (e.g., biomarker level), a condensation of the sequential representation (e.g., a combined signature based on multiple biomarkers), or a diagnosis, prognosis, or risk assessment, etc. In some embodiments, transformation involves conversion of data between any of the above.

Certain processes and methods described herein (e.g., data acquisition, data analysis, communication, etc.) are performed by (or cannot be performed without) a computer, processor, software, module and/or other device. Methods described herein typically are computer-implemented methods, and one or more portions of a method sometimes are performed by one or more processors. In some embodiments, an automated method is embodied in software, processors, peripherals and/or an apparatus comprising the like. As used herein, software refers to computer readable program instructions that, when executed by a processor, perform computer operations, as described herein.

The terms "obtaining," "transferring," "receiving," etc. refer to movement of data (e.g., raw data, biomarker levels, combined biomarker data, risk profile, signature, diagnosis, etc.) between modules, devices, apparatuses, etc. within a system. These terms may also refer to the handling of samples and purified versions thereof (e.g., with respect to amplification, purification, analysis, etc.). Input information may be generated in the same location at which it is received, or it may be generated in a different location and transmitted to the receiving location. In some embodiments, input information is modified before it is processed (e.g., placed into a format amenable to processing (e.g., tabulated)). In some embodiments, provided are computer program products, such as, for example, a computer program product comprising a computer usable medium having a computer readable program code embodied therein, the computer readable program code adapted to be executed to implement a method.

Software may include one or more algorithms in certain embodiments. An algorithm may be used for processing biomarker data, analyzing data, and/or providing an outcome or report according to a sequence of instructions. An algorithm often is a list of defined instructions for completing a task. Starting from an initial state, the instructions may describe a computation that proceeds through a defined series of successive states, eventually terminating in a final ending state. By way of example, and without limitation, an algorithm may be a search algorithm, sorting algorithm, merge algorithm, numerical algorithm, graph algorithm, string algorithm, modeling algorithm, computational geometric algorithm, combinatorial algorithm, machine learning algorithm, cryptography algorithm, data compression algorithm, parsing algorithm and the like. In some embodiments, an algorithm or set of algorithms transform data (e.g., biomarker) into information useful for solving a problem (e.g., identifying a subject as depressed or at-risk of depression). Algorithms utilized in embodiments herein make improvements in the fields of mental health, public health, medicine, diagnostic applications, diagnostic development, etc. In certain embodiments, algorithms may be implemented by software.

In some embodiments, the present invention contemplates screening arrays of compounds (e.g., pharmaceuticals, drugs, peptides, or other test compounds) for their ability to treat depression (e.g., MDD). In some embodiments, compounds (e.g., pharmaceuticals, drugs, peptides, or other test compounds) identified using screening assays of the present invention find use in the diagnosis or treatment of depression (e.g., MDD).

In some embodiments, the present invention provides screening assays for assessing cellular behavior or function. For example, the response of cells, tissues, or organisms to interventions (e.g., psychoanalysis (e.g., CBT, etc.), pharmaceutical treatment, etc.) may be monitored by assessing, for example, cellular functions using animal or cell culture models as described herein. Such assays find particular use for characterizing, identifying, validating, selecting, optimizing, or monitoring the effects of agents (e.g., small molecule-, peptide-, antibody-, nucleic acid-based drugs, etc.) that find use in treating or preventing depression, MDD, or related diseases or conditions.

Compositions for use in the diagnostic methods of the present invention include, but are not limited to, probes, amplification oligonucleotides, and antibodies. Particularly preferred compositions detect the level of expression of a panel of genes. Systems and kits are provided that are useful, necessary, and/or sufficient for detecting expression of one or more genes.

Any of these compositions, alone or in combination with other compositions of the present invention, may be provided in the form of a kit. For example, the single labeled probe and pair of amplification oligonucleotides may be provided in a kit for the amplification and detection and/or quantification of a panel of genes. The kit may include any and all components necessary or sufficient for assays including, but not limited to, the reagents themselves, buffers, control reagents (e.g., tissue samples, positive and negative control sample, etc.), solid supports, labels, written and/or pictorial instructions and product information, inhibitors, labeling and/or detection reagents, package environmental controls (e.g., ice, desiccants, etc.), and the like. In some embodiments, the kits provide a sub-set of the required components, wherein it is expected that the user will supply the remaining components. In some embodiments, the kits comprise two or more separate containers wherein each container houses a subset of the components to be delivered.

In some embodiments, the present invention provides therapies for diseases characterized by altered expression of disease markers identified using the methods of the present invention. In particular, the present invention provides methods and compositions for monitoring the effects of a candidate therapy and for selecting therapies for patients.

In some embodiments, methods of treating depression are provided (e.g., following detection/quantification of one or more of the biomarkers and/or panels described herein). Suitable treatments include psychotherapy; medication (e.g., selective serotonin reuptake inhibitors (SSRIs) (e.g., fluoxetine (Prozac), paroxetine (Paxil), sertraline (Zoloft), citalopram (Celexa) and escitalopram (Lexapro), etc.), serotonin and norepinephrine reuptake inhibitors (SNRIs) (e.g., duloxetine (Cymbalta), venlafaxine (Effexor XR) and desvenlafaxine (Pristiq), etc.), norepinephrine and dopamine reuptake inhibitors (NDRIs) (e.g., Bupropion (Wellbutrin), etc.), atypical antidepressants (e.g., trazodone, mirtazapine (Remeron), vilazodone (Viibryd), etc.), tricyclic antidepressants (e.g., imipramine (Tofranil) and nortriptyline (Pamelor), etc.), monoamine oxidase inhibitors (MAOIs) (e.g., tranylcypromine (Parnate), phenelzine (Nardil), etc.), mood stabilizers, antipsychotics, anti-anxiety medications, stimulant medications, etc.); hospitalization or residential treatment; electroconvulsive therapy (ECT); transcranial magnetic stimulation (TMS); etc.

In some embodiments, systems and devices are provided for implementing the diagnostic methods described herein (e.g., data analysis, communication, result reporting, etc.). In some embodiments, a software or hardware component receives the results of multiple assays, factors, and/or biomarkers and determines a single value result to report to a user that indicates a conclusion related to depression status. Related embodiments calculate a risk factor based on a mathematical combination (e.g., a weighted combination, a linear combination) of the results from multiple assays, factors, and/or biomarkers.

EXPERIMENTAL

Example 1

Identification of MDD Biomarkers

Experiments were conducted during the development of embodiments of the invention to identify biomarkers of MDD through genome-wide expression analysis in the blood and relevant brain regions of animal models of MDD developed from a well-accepted genetic animal model of depression, the Wistar Kyoto (WKY) rat strain. Two sub-strains were developed from the WKY strain that show opposite behavior in behavioral tests used to measure depression. The WKY More Immobile (WMI) line is more depressed while the WKY Less Immobile (WLI) line is less depressed. Since these sub-strains were developed from an inbred line, their genetic variability is very small, thereby indicating that expression differences in their brain and blood are related to the behavioral differences between them.

AFFYMETRIX microarray profiling of gene expression patterns, using the Rat 230v2 AFFYMETRIX GENECHIP arrays, were carried out in the frontal cortex, amygdale, hippocampus, and striatum in both WMI and WLI males. Microarray analysis was repeated from the same brain regions using different generation animals. Microarray profiling of gene expression patterns was also carried out in the blood of WMI and WLI males. Blood microarray analysis was repeated from the 20TH generation WMI-WLIs using ILLUMINA SENTRIX Rat (Ref-12) Expression BEAD-CHIP, version 1.0, release 1. Based on the analyses of these microarray data, a biomarker list was created using the data of blood and brain expression (Table 1).

Additional markers were identified from the chronic stress model of depression. The model employed young adult males of four phylogenetically, physiologically, and behaviorally different strains of rats: Fisher-344 (F344), Brown Norway (BN-SS), Lewis (Lew), and Wistar Kyoto (WKY) male rats. Half of the animals from each strain were exposed to chronic restraint stress, the other half were not. The chronically stressed animals were restrained in a breathable decapicone for two hours per day for a two-week period. For the determination of peripheral chronic stress markers, whole blood was collected into PAXgene tubes. Blood RNA from non-stressed and chronically stressed animals was isolated using the PAXgene Blood RNA Kit (Qiagen Inc.) according to the manufacturer's instruction, then reverse transcribed followed by second strand cDNA synthesis. For each sample, an in-vitro transcription reaction was carried out incorporating biotinylated nucleotides according to the manufacturer's protocol for Illumina® Totalprep RNA amplification kit (Ambion). Then, 1.5 µg biotin-labelled cRNA was hybridized onto RatRef-12 Expression BeadChips (Illumina, San Diego Calif.) for 16 hours at 55° C. Based on the analyses of these expression data, a biomarker list was created that comprised all the transcripts showing significant differences between the non-stressed and the stress blood of all strain of rats (Table 2).

TABLE 1

Candidate markers for endogenous MDD

| Gene Symbol | Gene name (number of transcripts) | Gene Symbol | Gene name (number of transcripts) |
|---|---|---|---|
| FAM46A | family with sequence similarity 46, member A (7) | NRP1 | neuropilin 1 (18) |
| MARCKS | myristoylated alanine-rich protein kinase C substrate (1) | PDE6D | phosphodiesterase 6D, cGMP-specific, rod, delta (6) |
| ATP2C1 | ATPase Ca++ transporting, type 2C, member 1 (6) | PPP1R3B | protein phosphatase 1, regulatory subunit 3B (1) |
| ATP11C | ATPase, class VI, type 11C | PRPF18 | PRP18 pre-mRNA processing factor 18 homolog (5) |
| NAGA | N-acetyl-galactosaminidase, alpha (5) | RAPH1 | Ras association (RalGDS/AF-6) and pleckstrin homology domains 1 |
| TLR7 | toll-like receptor 7 (2) | RNASEL | ribonuclease L (2) |
| ADCY3 | adenylate cyclase 3 (15) | SEMA4A | semaphorin 4A (16) |
| ANXA4 | annexin A4 (13) | SERPINB1 | serpin peptidase inhibitor, clade B, member 1 (5) |
| APP | amyloid beta(A4) precursor protein (20) | SLFN12 | schlafen family member 12 (8) |
| ASAH1 | N-acylsphingosine amidohydrolase 1 (4) | SMPDL3A | sphingomyelin phosphodiesterase, acid-like 3A (2) |
| ATP6AP2 | ATPase, H+ transporting, lysosomal accessory protein 2 (7) | SNX10 | sorting nexin 10 (8) |
| BCAT1 | branched chain aminotransferase 1, cytosolic (2) | SOAT1 | sterol O-acyltransferase 1 (2) |
| CAST | calpastatin (13) | SYNJ1 | synaptojanin 1 (19) |
| CD59 | CD59 molecule, complement regulatory protein (7) | TCF7L2 | transcription factor 7-like 2 (16) |
| CEBPA | CCAAT/enhancer binding protein, alpha (1) | ZNF291/ SCAPER | S-phase cyclin A-associated protein (2) |
| CITED2 | Cbp/p300-interacting transactivator, with Glu/Asp-rich carboxy-terminal domain, 2 (2) | FUCA2 | fucosidase, alpha-L-2, plasma (6) |
| FOS | FBJ murine osteosarcoma viral oncogene homolog (1) | DAG1 | dystrophin-associated glycoprotein 1 |
| IDH1 | isocitrate dehydrogenase 1 (NADP+), soluble (13) | MAF | v-maf oncogene homolog (2) |
| IGSF4AA/ CADM1 | cell adhesion molecule 1 (3) | GNAQ | guanine nucleotide binding protein alpha stimulating activity polypeptide 1 (2) |
| IL13RA1 | interleukin 13 receptor, alpha 1 (4) | MAST4 | microtubule associated serine/threonine kinase family member 4 (30) |
| KLF4 | Kruppel-like factor 4 (8) | FMR1 | fragile X mental retardation 1 (13) |
| LRRC40 | leucine rich repeat containing 40 (1) | PTPRM | protein tyrosine phosphatase, receptor type, mu polypeptide (4) |

TABLE 2

Chronic stress blood markers

| Gene symbol | Gene name | Gene symbol | Gene name |
|---|---|---|---|
| ADD2 | adducin 2 | KIAA1539 | KIAA1539 |
| ADIPOR1 | adiponectin receptor 1 | LEPROTL1 | leptin receptor overlap transcript-like 1 |
| ARF5 | ADP-ribosylation factor 5 | LAPTM5 | lysosomal-associated protein transmembrane 5 |

TABLE 2-continued

Chronic stress blood markers

| Gene symbol | Gene name | Gene symbol | Gene name |
|---|---|---|---|
| AHSP | alpha hemoglobin stabilizing protein (ERAF) | MTVR2 | mammary tumor virus receptor 2 |
| ANK1 | ankyrin 1, erythroid | MXD1 | max dimerization protein 1 |
| APOL3 | apolipoprotein L, 3 | MEMO1 | mediator of cell motility 1 |
| ARIH1 | ariadne ubiquitin-conjugating enzyme E2 binding protein homolog 1 | MIIP | migration and invasion inhibitory protein |
| AMFR | autocrine motility factor receptor | MAP2K3 | mitogen activated protein kinase kinase 3 |
| BOLA3 | bolA homolog 3 | NAT9 | N-acetyltransferase 9 |
| CHP | calcium binding protein p22 | NBEAL2-PS1 | neurobeachin-like 2, pseudogene 1 |
| CA2 | carbonic anhydrase 2 | NXT1 | NTF2-related export protein 1 |
| CA1 | carbonic anhydrase I | NOP56 | nucleolar protein 56 |
| CSNK1G2 | casein kinase 1, gamma 2 | PCYT2 | phosphate cytidylyltransferase 2, ethanolamine |
| CAT | catalase | PLCG2 | phospholipase C, gamma 2 |
| CTSB | cathepsin B | PARP10 | poly (ADP-ribose) polymerase family, member 10 |
| CD3D | CD3 antigen delta polypeptide | KTCD20 | potassium channel tetramerisation domain containing 20 |
| CD37 | CD37 antigen | PAQR9 | progestin and adipoQ receptor family member IX |
| CD82 | CD82 antigen | PSME1 | protease 28 subunit, alpha |
| CREG1 | cellular repressor of E1A-stimulated genes | PSMB10 | proteasome subunit, beta type 10 |
| CDR2 | cerebellar degeneration-related 2 | PSMB3 | proteasome subunit, beta type 3 |
| C7orf70 | chromosome 7 open reading frame 70 | PSMB8 | proteasome subunit, beta type 8 |
| C2 | complement component 2 | PPP1R10 | protein phosphatase 1, subunit 10 |
| CXXC1 | CXXC finger 1 | PTP4A3 | protein tyrosine phosphatase 4a3 |
| CMAS | cytidine monophospho-N-acetylneuraminic acid synthetase | RAB10 | member RAS oncogene family |
| DDX24 | DEAD box polypeptide 24 | RTP4 | receptor (chemosensory) transporter protein 4 |
| DENND5A | DENN/MADD domain containing 5A | MAF1 | Repressor of RNA polymerase III transcription MAF1 homolog |
| DGKA | diacylglycerol kinase, alpha | SELO | selenoprotein O |
| DNAJB6 | DnaJ homolog, subfamily B, member 6 | SEPT1 | septin 1 |
| DYRK3 | dual-specificity tyrosine-- phosphorylation regulated kinase 3 | SERBP1 | SERPINE1 mRNA binding protein 1 |
| DYNC1H1 | dynein, cytoplasmic, heavy chain 1 | SHARPIN | shank-interacting protein |
| DYNLL1 | dynein, cytoplasmic, light chain 1 | SMAP2 | small ArfGAP2 |
| EMB | embigin | SLC16A10 | solute carrier family 16, member 10 |
| EPB42 | erythrocyte membrane protein band 4.2 | SLC4A1 | solute carrier family 4, member 1 |
| FBXO7 | F-box only protein 7 | SPTAN1 | spectrin, alpha, non-erythrocytic 1 |
| FAM117A | family with sequence similarity 117, member A | SYK | spleen tyrosine kinase |
| FAM125A | family with sequence similarity 125, member A | ST3GAL2 | ST3 beta-galactoside alpha-2,3-sialyltransferase 2 |
| FECH | ferrochelatase | STRADB | STE20-related kinase adaptor beta |
| FLNA | Filamin A | STRA8 | stimulated by retinoic acid gene 8 |
| FMNL1 | formin-like 1 | TSPAN8 | tetraspanin 8 |
| FN3K | fructosamine-3-kinase | TREX1 | 3-5 exonuclease TREX1 |
| FUS | fusion in malignant liposarcoma) | ATP5G1 | ATP synthase, H+ transporting, mitochondrial F0 complex, subunit c, isoform 1 |
| FYN | fyn proto-oncogene | TMCC2 | transmembrane and coiled-coil domain family 2 |

TABLE 2-continued

Chronic stress blood markers

| Gene symbol | Gene name | Gene symbol | Gene name |
| --- | --- | --- | --- |
| GATA1 | GATA binding protein 1 | TMEM183A | transmembrane protein 183A |
| GCLM | glutamate cysteine ligase, modifier subunit | TRIM10 | tripartite motif-containing 10 |
| ERICH1 | glutamate-rich 1 | TMOD1 | tropomodulin 1 |
| GLRX5 | glutaredoxin 5 | TINAGL1 | tubulointerstitial nephritis antigen-like 1 |
| GPX4 | glutathione peroxidase 4 | TIE1 | tyrosine kinase receptor 1 |
| GLTP | Glycolipid transfer protein | UBAC1 | ubiquitin associated domain containing 1 |
| GLG1 | golgi apparatus protein 1 | USP8 | ubiquitin specific protease 8 |
| GGA3 | golgi associated, gamma adaptin ear containing, ARF binding protein 3 | UBE2C | ubiquitin-conjugating enzyme E2C |
| GCH1 | GTP cyclohydrolase 1 | UBE2O | ubiquitin-conjugating enzyme E2O |
| HPS1 | Hermansky-Pudlak syndrome 1 homolog | UBE2R2 | ubiquitin-conjugating enzyme E2R 2 |
| SUV420H2 | histone-lysine N-methyltransferase | UROD | uroporphyrinogen decarboxylase |
| HAGH | hydroxyacyl glutathione hydrolase | VAMP3 | vesicle-associated membrane protein 3 |
| INSL3 | insulin-like 3 | VKORC1L1 | vitamin K epoxide reductase complex, subunit 1-like 1 |
| IRF3 | interferon regulatory factor 3 | WDR26 | WD repeat domain 26 |
| IFRD2 | interferon-related developmental regulator 2 | WDR45 | WD repeat domain 45 |
| ISG12 | interferon, alpha-inducible protein 27-like | ZAP70 | zeta-chain associated protein kinase 70 kDa |
| ISCU | iron-sulfur cluster scaffold homolog | | |

Example 2

Experiments using human subjects were conducted to identify human biomarkers of MDD.

Recruitment and Procedures

Participants were recruited from Northwestern General Internal Medicine clinics and were included if they were ≥18 years old, could speak and read English and provided informed consent. MDD subjects met criteria for MDD based on the Mini International Neuropsychiatry Interview (MINI), had a Hamilton Depression Rating Scale (Ham-D) (Hamilton. Journal of Neurology, Neurosurgery, and Psychiatry 1960; 23: 56-62.; herein incorporated by reference in its entirety) score ≥16 and were able to participate in face-to-face or telephone therapy. Non-depressed controls matched by age, race and sex, were recruited with the help of NUgene (Northwestern Medicine, Northwestern University) and included if they did not meet criteria for depression and scored <four on Patient Health Questionnaire-9 (PHQ-9).

Participants were excluded if they: 1) had visual or hearing impairments; 2) met diagnostic criteria for other psychiatric disorder (e.g. bipolar disorder, psychotic disorders, etc.) or depression of organic etiology (e.g. hypothyroidism); 3) reported alcohol or substance abuse severe enough that two psychologists agreed psychotherapy would be inappropriate, 4) met criteria for dementia by scoring <25 on the Telephone Interview for Cognitive Status (Desmond et al. International journal of geriatric psychiatry 1994; 9: 803-7.; herein incorporated by reference in its entirety); 5) exhibited severe suicidality, including a plan and intent, or a suicide attempt in the past 5 years; 6) were receiving or planning to receive individual psychotherapy; or 7) had initiated antidepressant pharmacotherapy in the previous 10 days. This trial was approved by the Northwestern University IRB and was monitored by an independent data safety monitoring board.

MDD diagnosis was evaluated at baseline using the MINI. Depression severity was evaluated by self-report using the PHQ-9. The PHQ-9 was selected because the items map onto diagnostic criteria for MDD and are, therefore, specific to depression. Venous blood (2.5 ml) was collected into PAXgene™ Blood RNA tubes (Qiagen, Germantown, Md.) for RNA analysis both at baseline and post-treatment from subject with MDD and at baseline from ND controls.

Determination of Blood Transcript Levels of Candidate Markers

Blood RNA was extracted using the PAXgene™ Blood RNA Kit (Qiagen, Germantown, Md.), according to the manufacturer's protocol. The yield and quality of extracted RNA were assessed using the NanoDrop™ 1000 spectrophotometer (NanoDrop Technologies, Wilmington, Del.). cDNA was prepared using random primers and the TaqMan RT reagents (ABI). Specific primers are listed in Table 3, some of which were reported previously.

TABLE 3

Primer sequences for qPCR

| Gene symbol | Forward Primer Sequence 5'→3' | Reverse Primer Sequence 5'→3' | Amplicon Length (bp) |
|---|---|---|---|
| ADCY3 | CGAGAACGTCAGCATCCTCTTT (SEQ ID NO. 1) | GGCACTGCAGGCAGAAGAC (SEQ ID NO. 2) | 66 |
| AMFR | CCTACACAGCGGTCAGATAGCAT (SEQ ID NO. 3) | TCACTGCTTGGCCTTTCCA (SEQ ID NO. 4) | 65 |
| ASAH1 | TCAACAAGCTGACCGTATACACA (SEQ ID NO. 5) | CCCGCAGGTAAGTTTCGAATT (SEQ ID NO. 6) | 68 |
| ATP11C | TCCATCAGTGGTGCAAGATG (SEQ ID NO. 7) | TTGAAAATGCAAAGCGAGTG (SEQ ID NO. 8) | 125 |
| CD59 | CCAAAGCTGGGTTACAAGTGTATAAC (SEQ ID NO. 9) | GTGACGTCGTTGAAATTGCAA (SEQ ID NO. 10) | 67 |
| CDR2 | CCGCCAACACTTCGTGTATG (SEQ ID NO. 11) | TCAGGGCTTGGCTGACCTT (SEQ ID NO. 12) | 72 |
| CMAS | ATCTTGGAAATGAAGTGTCTGATGAA (SEQ ID NO. 13) | GCAGGAGCGCCACTTAGG (SEQ ID NO. 14) | 64 |
| DGKA | ACCCTTCCCATGCAAATTGA (SEQ ID NO. 15) | CTTGTGGGTGATCTTGATTGTACAG (SEQ ID NO. 16) | 69 |
| FAM46A | CTCACGCTCAAGGAAGCTTATGT (SEQ ID NO. 17) | GGATATAAGACTCCATCGGTCAGAGT (SEQ ID NO. 18) | 75 |
| IGSF4A | AGCAAGCCAGCCACGACTAT (SEQ ID NO. 19) | CGATTTGCCTTTTAGCTCTGTGT (SEQ ID NO. 20) | 60 |
| KIAA1539 | CCGTCCAAGTGACCTTATTTAACC (SEQ ID NO. 21) | AGAAGTCAAAGGTCACAAGGAACAT (SEQ ID NO. 22) | 69 |
| MAF | CAGCGGCTTCCGAGAAAAC (SEQ ID NO. 23) | GAGTGGGCTCAGTTATGAAAAACTC (SEQ ID NO. 24) | 74 |
| MARCKS | CCTCTTGGATCTGTTGAGTTTCTTT (SEQ ID NO. 25) | ATTCTCCTGTCCGTTCGCTTT (SEQ ID NO. 26) | 148 |
| NAGA | AGCTGAGACCAAAGTTCCCA (SEQ ID NO. 27) | ATCCTGAATTGGTTCGTGGA (SEQ ID NO. 28) | 106 |
| PSME1 | CCGCAATGCTTATGCTGTGT (SEQ ID NO. 29) | GGGCTTCTTGAGCTTCTCGAA (SEQ ID NO. 30) | 64 |
| PTP4A3 | CCCTTATTGAGAGCGGGATGA (SEQ ID NO. 31) | CGCTTCTGGCGGATGAAC (SEQ ID NO. 32) | 58 |
| RAPH1 | AGCAAGGCCAGAATGGAGTCTAT (SEQ ID NO. 33) | GTGGTGAAGGCTGTGAAGCA (SEQ ID NO. 34) | 109 |
| SLC4A1 | GGAGCTTCAGTGTCTGGATGCT (SEQ ID NO. 35) | CGTATTCATCCCGACCTTCCT (SEQ ID NO. 36) | 71 |
| TLR7 | GCTCTCTTCAACCAGACCTCTACAT (SEQ ID NO. 37) | GTCCACATTGGAAACACCATTTT (SEQ ID NO. 38) | 68 |
| ZNF291 | GCACTCATAAAACTACTAAACAGCAGAGT (SEQ ID NO. 39) | TGTTTATCTCCAGTCGTAGACGATGT (SEQ ID NO. 40) | 76 |

Quantitative real time PCR (qPCR) was carried out using SYBR Green and the ABI 7900 (Applied Biosystems, Foster City, Calif.), with 18s rRNA as the internal control. 18s was chosen as the normalizing gene after an extensive comparative pilot study using several housekeeping genes (data not shown). Each sample for each transcript was measured in triplicate using 5 ng of template.

Baseline samples, collected from 32 patients with current MDD episode and 32 ND subjects, were analyzed in parallel. ΔCT values from qPCR characterized transcript abundance, where ΔCT is the cycle threshold difference between the target gene and the housekeeping gene. Then, to avoid inter-assay variations, the triads we re-assayed: baseline MDD, post CBT MDD and ND samples. In the statistical analyses of these results, either MDD and ND transcript levels were compared using the ΔCT values, or the control matching design and this relative quantification number (RQ) was used.

Statistical Analyses

Baseline PHQ-9 and ΔCT transcript levels were compared between MDD and ND using paired t-tests, and presented with mean and standard deviation. To avoid inflated type I errors, false discovery rates (Benjamini & Hochberg. J Roy Stat Soc B Met 1995; 57: 289-300.; herein incorporated by reference in its entirety) were estimated by q-values using the q-value package in R (Storey & Tibshirani. Proceedings of the National Academy of Sciences 2003; 100: 9440-5.; Team RC. R: A language and environment for statistical computing. ISBN 3-900051-07-0. R Foundation for Statistical Computing. Vienna, Austria, 2013. url: http://www.R-project.org; 2005.; herein incorporated by reference in their entireties). An a priori decision was made to interpret significant q values and an effect size of >0.45 as clinically significant, which corresponds to Cohen's medium effect size (Cohen J. Statistical Power Analysis for the Behavioral Sciences. 2nd ed. Hillsdale: L Erlbaum Associates; 1988.; herein incorporated by reference in its entirety).

Transcript Level Differences at Baseline

Levels of twenty transcripts were measured at baseline (Tables 4). Blood transcript levels differed between subjects with MDD from their age-, sex- and race-matched ND controls for adenylate cyclase 3 (ADCY3), diacylglycerol kinase, alpha (DGKA), family with sequence similarity 46, member A (FAM46A), immunoglobulin superfamily, member 4 (IGSF4A/CADM1) also known as cell adhesion molecule 1 (CADM1), KIAA1539, which either have no brain-related functions to date or no known function, myristoylated alanine-rich protein kinase C substrate (MARCKS), proteasome activator subunit 1 (PSME1), Ras association and pleckstrin homology domains 1 also known as LPD (RAPH1) and intracellular toll-like receptor 7 (TLR7).

TABLE 4

Baseline transcript levels (ΔCT) for subjects with MDD (N = 32) and sex, age, race matched ND controls (N = 32).

| Gene | MDD Mean (SD) | CONTROL Mean (SD) | p-value | q | Cohen's D |
|---|---|---|---|---|---|
| ADCY3 | 20.95 (2.07) | 21.31 (2.18) | 0.012 | 0.026 | 0.473 |
| AMFR | 19.28 (0.87) | 19.27 (0.42) | 0.995 | 0.995 | 0.001 |
| ASAH1 | 16.74 (2.45) | 16.88 (2.25) | 0.352 | 0.503 | 0.167 |
| ATP11C | 19.22 (1.83) | 19.20 (2.17) | 0.902 | 0.949 | 0.022 |
| CD59 | 19.98 (0.65) | 19.89 (0.66) | 0.550 | 0.651 | 0.107 |
| CDR2 | 20.60 (1.13) | 20.49 (0.65) | 0.554 | 0.652 | 0.106 |
| CMAS | 22.41 (1.36) | 22.98 (0.69) | 0.046 | 0.084 | 0.367 |
| DGKA | 16.69 (0.80) | 17.41 (0.75) | 0.000 | 0.003 | 0.730 |
| FAM46A | 19.65 (2.27) | 19.96 (2.40) | 0.005 | 0.017 | 0.532 |
| IGSF4A/CADM1 | 22.22 (3.07) | 23.05 (2.57) | 0.002 | 0.010 | 0.597 |
| KIAA1539 | 18.22 (0.61) | 18.64 (0.45) | 0.001 | 0.009 | 0.625 |
| MAF | 22.00 (2.31) | 22.08 (2.47) | 0.637 | 0.708 | 0.084 |
| MARCKS | 16.85 (2.31) | 17.41 (2.22) | 0.005 | 0.017 | 0.533 |
| NAGA | 17.63 (2.22) | 17.85 (2.30) | 0.041 | 0.083 | 0.376 |
| PSME1 | 17.17 (0.75) | 17.55 (0.52) | 0.008 | 0.023 | 0.501 |
| PTP4A3 | 20.79 (0.82) | 21.03 (0.62) | 0.154 | 0.257 | 0.258 |
| RAPH1 | 21.73 (1.47) | 22.80 (0.54) | <0.001 | 0.003 | 0.737 |
| SLC4A1 | 17.08 (0.85) | 17.22 (0.85) | 0.454 | 0.606 | 0.134 |
| TLR7 | 19.53 (2.36) | 19.89 (2.35) | 0.009 | 0.023 | 0.493 |
| ZNF291 | 23.55 (3.18) | 23.20 (3.20) | 0.176 | 0.270 | 0.253 |

Scatter plots of delta CT values for each transcript measured at baseline in MDD subjects and their matched controls are presented in FIG. 1.

All publications and patents listed below and/or provided herein incorporated by reference in their entireties. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

REFERENCES

1. Kessler R C, Berglund P, Demler O, Jin R, Merikangas K R, Walters E E. Lifetime prevalence and age-of-onset distributions of DSM-IV disorders in the National Comorbidity Survey Replication. Arch Gen Psychiatry 2005; 62: 593-602.
2. Hidaka B H. Depression as a disease of modernity: explanations for increasing prevalence. J Affect Disord 2012; 140: 205-14.
3. Lepine J P, Briley M. The increasing burden of depression. Neuropsychiatr Dis Treat 2011; 7: 3-7.
4. Ferrari A J, Charlson F J, Norman R E, Patten S B, Freedman G, Murray C J, et al. Burden of depressive disorders by country, sex, age, and year: findings from the global burden of disease study 2010. PLoS Med 2013; 10: e1001547.
5. Hardeveld F, Spijker J, De Graaf R, Nolen W A, Beekman A T. Prevalence and predictors of recurrence of major depressive disorder in the adult population. Acta psychiatrica Scandinavica 2010; 122: 184-91.
6. ten Doesschate M C, Bockting C L, Koeter M W, Schene A H. Prediction of recurrence in recurrent depression: a 5.5-year prospective study. J Clin Psychiatry 2010; 71: 984-91.
7. Carter J D, Frampton C M, Mulder R T, Luty S E, Joyce P R. The relationship of demographic, clinical, cognitive and personality variables to the discrepancy between self and clinician rated depression. J Affect Disord 2010; 124: 202-6.
8. Riedel M, Moller H J, Obermeier M, Schennach-Wolff R, Bauer M, Adli M, et al. Response and remission criteria in major depression—a validation of current practice. J Psychiatr Res 2010; 44: 1063-8.
9. Belmaker R H, Agam G. Major depressive disorder. The New England journal of medicine 2008; 358: 55-68.
10. Altamura A C, Buoli M, Albano A, Dell'Osso B. Age at onset and latency to treatment (duration of untreated illness) in patients with mood and anxiety disorders: a naturalistic study. Int Clin Psychopharmacol 2010; 25: 172-9.
11. Huerta-Ramirez R, Bertsch J, Cabello M, Roca M, Haro J M, Ayuso-Mateos J L. Diagnosis delay in first episodes of major depression: a study of primary care patients in Spain. J Affect Disord 2013; 150: 1247-50.
12. Pence B W, O'Donnell J K, Gaynes B N. The depression treatment cascade in primary care: a public health perspective. Curr Psychiatry Rep 2012; 14: 328-35.
13. Andrus B M, Blizinsky K, Vedell P T, Dennis K, Shukla P K, Schaffer D J, et al. Gene expression patterns in the hippocampus and amygdala of endogenous depression and chronic stress models. Molecular psychiatry 2012; 17: 49-61.
14. Pajer K, Andrus B M, Gardner W, Lourie A, Strange B, Campo J, et al. Discovery of blood transcriptomic markers for depression in animal models and pilot validation in subjects with early-onset major depression. Transl Psychiatry 2012; 2: e101.
15. Mohr D C, Ho J, Duffecy J, Reifler D, Sokol L, Burns M N, et al. Effect of telephone-administered vs face-to-face cognitive behavioral therapy on adherence to therapy 15. and depression outcomes among primary care patients: a randomized trial. JAMA: the journal of the American Medical Association 2012; 307: 2278-85.
16. Mohr D C, Vella, L., Hart, S. L., Heckman, T., Simon, G. E. The effect of telephone-administered psychotherapy on depression and attrition: A meta-analysis. Clin Psych Sci & Pract 2012; 307: 2278-85.
17. Sheehan D V, Lecrubier Y, Sheehan K H, Amorim P, Janays J, Weiller E, et al. The Mini-International Neuropsychiatric Interview (M.I.N.I.): the development and validation of a structured diagnostic psychiatric interview for DSM-IV and ICD-10. J Clin Psychiatry 1998; 59 Suppl 20: 22-33; quiz 4-57.
18. Hamilton M. A rating scale for depression. Journal of Neurology, Neurosurgery, and Psychiatry 1960; 23: 56-62.
19. Desmond D W, Tatemichi T K, Hanzawa L. The Telephone Interview for Cognitive Status (TICS): Reliability and validity in a stroke sample. International journal of geriatric psychiatry 1994; 9: 803-7.
20. MacArthur Foundation's Initiative on Depression and Primary Care. The MacArthur Initiative on Depression and Primary Care at Dartmouth and Duke: Depression Management Toolkit. Hanover, N H: Dartmouth; 2004.
21. Benjamini Y, Hochberg Y. Controlling the False Discovery Rate—a Practical and Powerful Approach to Multiple Testing. J Roy Stat Soc B Met 1995; 57: 289-300.
22. Storey J D, Tibshirani R. Statistical significance for genomewide studies. Proceedings of the National Academy of Sciences 2003; 100: 9440-5.
23. Team R C. R: A language and environment for statistical computing. ISBN 3-900051-07-0. R Foundation for Statistical Computing. Vienna, Austria, 2013. url:http://www.R-project.org; 2005.
24. Cohen J. Statistical Power Analysis for the Behavioral Sciences. 2nd ed. Hillsdale: L Erlbaum Associates; 1988.
25. Pepe M, Longton G, Janes H. Estimation and Comparison of Receiver Operating Characteristic Curves. Stata J 2009; 9: 1.
26. Mehta D, Menke A, Binder E B. Gene expression studies in major depression. Curr Psychiatry Rep 2010; 12: 135-44.
27. Liew C C, Ma J, Tang H C, Zheng R, Dempsey A A. The peripheral blood transcriptome dynamically reflects system wide biology: a potential diagnostic tool. J Lab Clin Med 2006; 147: 126-32.
28. Rollins B, Martin M V, Morgan L, Vawter M P. Analysis of whole genome biomarker expression in blood and brain. Am J Med Genet B Neuropsychiatr Genet 2010; 153B: 919-36.
29. Sullivan P F, Fan C, Perou C M. Evaluating the comparability of gene expression in blood and brain. Am J Med Genet B Neuropsychiatr Genet 2006; 141B: 261-8.
30. Kurian S M, Le-Niculescu H, Patel S D, Bertram D, Davis J, Dike C, et al. Identification of blood biomarkers for psychosis using convergent functional genomics. Molecular psychiatry 2011; 16: 37-58.
31. Le-Niculescu H, Kurian S M, Yehyawi N, Dike C, Patel S D, Edenberg H J, et al. Identifying blood biomarkers for mood disorders using convergent functional genomics. Molecular psychiatry 2009; 14: 156-74.
32. Padmos R C, Hillegers M H, Knijff E M, Vonk R, Bouvy A, Staal F J, et al. A discriminating messenger RNA signature for bipolar disorder formed by an aberrant expression of inflammatory genes in monocytes. Arch Gen Psychiatry 2008; 65: 395-407.
33. Menke A, Arloth J, Putz B, Weber P, Klengel T, Mehta D, et al. Dexamethasone stimulated gene expression in peripheral blood is a sensitive marker for glucocorticoid receptor resistance in depressed patients. Neuropsychopharmacology: official publication of the American College of Neuropsychopharmacology 2012; 37: 1455-64.
34. Segman R H, Goltser-Dubner T, Weiner I, Canetti L, Galili-Weisstub E, Milwidsky A, et al. Blood mononuclear cell gene expression signature of postpartum depression. Molecular psychiatry 2010; 15: 93-100, 2.
35. Spijker S, Van Zanten J S, De Jong S, Penninx B W, van Dyck R, Zitman F G, et al. Stimulated gene expression profiles as a blood marker of major depressive disorder. Biological psychiatry 2010; 68: 179-86.
36. Papakostas G I, Shelton R C, Kinrys G, Henry M E, Bakow B R, Lipkin S H, et al. Assessment of a multiassay, serum-based biological diagnostic test for major depressive disorder: a pilot and replication study. Molecular psychiatry 2013; 18: 332-9.
37. Shyn S I, Shi J, Kraft J B, Potash J B, Knowles J A, Weissman M M, et al. Novel loci for major depression identified by genome-wide association study of Sequenced Treatment Alternatives to Relieve Depression and meta-analysis of three studies. Molecular psychiatry 2011; 16: 202-15.
38. Cross-Disorder Group of the Psychiatric Genomics Consortium. Identification of risk loci with shared effects on five major psychiatric disorders: a genome-wide analysis. Lancet 2013; 381: 1371-9.
39. Wray N R, Pergadia M L, Blackwood D H R, Penninx B W J H, Gordon S D, Nyholt D R, et al. Genome-wide association study of major depressive disorder: new results, meta-analysis, and lessons learned. Molecular psychiatry 2012; 17: 36-48.
40. Liotti M, Mayberg H S, McGinnis S, Brannan S L, Jerabek P. Unmasking disease-specific cerebral blood flow abnormalities: mood challenge in patients with remitted unipolar depression. Am J Psychiatry 2002; 159: 1830-40.
41. Segal Z V, Bieling P, Young T, MacQueen G, Cooke R, Martin L, et al. Antidepressant monotherapy vs sequential pharmacotherapy and mindfulness-based cognitive therapy, or placebo, for relapse prophylaxis in recurrent depression. Arch Gen Psychiatry 2010; 67: 1256-64.
42. Belzeaux R, Bergon A, Jeanjean V, Loriod B, Formisano-Treziny C, Verrier L, et al. Responder and nonresponder patients exhibit different peripheral transcriptional signatures during major depressive episode. Transl Psychiat 2012; 2.
43. Gaiteri C, Ding Y, French B, Tseng G C, Sibille E. Beyond modules and hubs: the potential of gene coexpression networks for investigating molecular mechanisms of complex brain disorders. Genes, brain, and behavior 2014; 13: 13-24.
44. Menke A. Gene expression: biomarker of antidepressant therapy? Int Rev Psychiatry 2013; 25: 579-91.
45. Gunther E C, Stone D J, Gerwien R W, Bento P, Heyes M P. Prediction of clinical drug efficacy by classification of drug-induced genomic expression profiles in vitro. Proceedings of the National Academy of Sciences of the United States of America 2003; 100: 9608-13.
46. Leuchter A F, Cook I A, Marangell L B, Gilmer W S, Burgoyne K S, Howland R H, et al. Comparative effectiveness of biomarkers and clinical indicators for predicting outcomes of SSRI treatment in Major Depressive Disorder: results of the BRITE-M D study. Psychiatry Res 2009; 169: 124-31.

47. Cuijpers P, Karyotaki E, Weitz E, Andersson G, Hollon S D, van Straten A. The effects of psychotherapies for major depression in adults on remission, recovery and improvement: A meta-analysis. J Affect Disorders.
48. Licinio J, Wong M L. Pharmacogenomics of antidepressant treatment effects. Dialogues Clin Neurosci 2011; 13: 63-71.
49. Licinio J, Wong M L. Launching the 'war on mental illness'. Molecular psychiatry 2014; 19: 1-5.
50. Radich J P, Mao M, Stepaniants S, Biery M, Castle J, Ward T, et al. Individual-specific variation of gene expression in peripheral blood leukocytes. Genomics 2004; 83: 980-8.
51. Eady J J, Wortley G M, Wormstone Y M, Hughes J C, Astley S B, Foxall R J, et al. Variation in gene expression profiles of peripheral blood mononuclear cells from healthy volunteers. Physiological genomics 2005; 22: 402-11.
52. Mohr S, Liew C-C. The peripheral-blood transcriptome: new insights into disease and risk assessment. Trends in Molecular Medicine 2007; 13: 422-32.

I claim:

1. A panel of biomarkers consisting of an isolated set of 100 or fewer full-length cDNA biomarkers, wherein said isolated set includes ADCY3, DGKA, FAM46A, IGSF4A/ CADM1, KIAA1539, MARCKS, PSME1, RAPH1, and TLR7 full-length cDNA biomarkers.

* * * * *